US008858782B2

(12) United States Patent
Fife

(10) Patent No.: US 8,858,782 B2
(45) Date of Patent: Oct. 14, 2014

(54) ION-SENSING CHARGE-ACCUMULATION CIRCUITS AND METHODS

(75) Inventor: Keith Fife, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/173,146

(22) Filed: Jun. 30, 2011

(65) Prior Publication Data

US 2012/0000274 A1    Jan. 5, 2012

Related U.S. Application Data

(60) Provisional application No. 61/360,493, filed on Jun. 30, 2010, provisional application No. 61/360,495, filed on Jul. 1, 2010, provisional application No. 61/361,403, filed on Jul. 3, 2010.

(51) Int. Cl.
   *G01N 27/414* (2006.01)
(52) U.S. Cl.
   CPC .......... *G01N 27/4148* (2013.01); *G01N 27/414* (2013.01); *G01N 27/4145* (2013.01)
   USPC .......... 205/793.5; 205/792; 257/253
(58) Field of Classification Search
   USPC .............. 257/253; 205/793.5, 782
   See application file for complete search history.

(56) References Cited

U.S. PATENT DOCUMENTS

| | | | |
|---|---|---|---|
| 4,086,642 A | 4/1978 | Yoshida et al. | |
| 4,411,741 A | 10/1983 | Janata | |
| 4,437,969 A | 3/1984 | Covington et al. | |
| 4,490,678 A | 12/1984 | Kuisl et al. | |
| 4,641,084 A | 2/1987 | Komatsu | |

(Continued)

FOREIGN PATENT DOCUMENTS

| | | |
|---|---|---|
| CN | 102203282 | 9/2011 |
| DE | 19512117 | 10/1996 |

(Continued)

OTHER PUBLICATIONS

[No Author Listed], "ISFET Wikipedia article", *Wikipedia*, Last modified Nov. 7, 2006, 2006.

(Continued)

*Primary Examiner* — Bach Dinh

(57) ABSTRACT

An ion-sensitive circuit can include a charge accumulation device, to accumulate a plurality of charge packets as a function of an ion concentration of a fluid, and at least one control and readout transistor, to generate an output signal as a function of the accumulated plurality of charge packets, the output signal representing the ion concentration of the solution. The charge accumulation device can include a first charge control electrode above a first electrode semiconductor region, an electrically floating gate structure above a gate semiconductor region and below an ion-sensitive passivation surface, a second charge control electrode above a second electrode semiconductor region, and a drain diffusion region. The first control electrode can control entry of charge into a gate semiconductor region in response to a first control signal. The ion-sensitive passivation surface can be configured to receive the fluid. The second charge control electrode can control transmission of the plurality of charge packets out of the gate semiconductor region and into the drain diffusion region in response to a second control signal. The drain diffusion region can receive the plurality of charge packets from the gate semiconductor region via the second electrode semiconductor region.

14 Claims, 7 Drawing Sheets

(56) References Cited

U.S. PATENT DOCUMENTS

| | | | |
|---|---|---|---|
| 4,660,063 | A | 4/1987 | Anthony |
| 4,691,167 | A | 9/1987 | Vlekkert et al. |
| 4,701,253 | A | 10/1987 | Litenberg et al. |
| 4,722,830 | A | 2/1988 | Urie et al. |
| 4,743,954 | A | 5/1988 | Brown |
| 4,764,797 | A | 8/1988 | Shaw et al. |
| 4,777,019 | A | 10/1988 | Dandekar |
| 4,822,566 | A | 4/1989 | Newman |
| 4,863,849 | A | 9/1989 | Melamede |
| 4,864,229 | A | 9/1989 | Lauks et al. |
| 4,874,499 | A | 10/1989 | Smith et al. |
| 4,971,903 | A | 11/1990 | Hyman |
| 5,009,766 | A | 4/1991 | Lauks |
| 5,038,192 | A | 8/1991 | Bonneau et al. |
| 5,110,441 | A | 5/1992 | Kinlen et al. |
| 5,113,870 | A | 5/1992 | Rossenfeld |
| 5,138,251 | A | 8/1992 | Koshiishi et al. |
| 5,151,759 | A | 9/1992 | Vinal |
| 5,164,319 | A | 11/1992 | Hafeman et al. |
| 5,284,566 | A | 2/1994 | Cuomo et al. |
| 5,317,407 | A | 5/1994 | Michon |
| 5,319,226 | A | 6/1994 | Sohn et al. |
| 5,407,854 | A | 4/1995 | Baxter et al. |
| 5,436,149 | A | 7/1995 | Barnes |
| 5,439,839 | A | 8/1995 | Jang |
| 5,466,348 | A | 11/1995 | Holm-Kennedy |
| 5,490,971 | A | 2/1996 | Gifford et al. |
| 5,554,339 | A | 9/1996 | Cozzette et al. |
| 5,583,462 | A | 12/1996 | Grasshoff |
| 5,593,838 | A | 1/1997 | Zanzucchi et al. |
| 5,600,451 | A | 2/1997 | Maki |
| 5,631,704 | A | 5/1997 | Dickinson et al. |
| 5,637,469 | A | 6/1997 | Wilding et al. |
| 5,702,964 | A | 12/1997 | Lee |
| 5,793,230 | A | 8/1998 | Chu et al. |
| 5,846,708 | A | 12/1998 | Hollis et al. |
| 5,911,873 | A | 6/1999 | McCarron et al. |
| 5,912,560 | A | 6/1999 | Pasternak |
| 5,922,591 | A | 7/1999 | Anderson et al. |
| 5,923,421 | A | 7/1999 | Rajic et al. |
| 5,958,703 | A | 9/1999 | Dower et al. |
| 5,965,452 | A | 10/1999 | Kovacs |
| 6,002,299 | A | 12/1999 | Thomsen |
| 6,107,032 | A | 8/2000 | Kilger et al. |
| 6,195,585 | B1 | 2/2001 | Karunasiri et al. |
| 6,210,891 | B1 | 4/2001 | Nyren et al. |
| 6,255,678 | B1 | 7/2001 | Sawada et al. |
| 6,274,320 | B1 | 8/2001 | Rothberg et al. |
| 6,327,410 | B1 | 12/2001 | Walt et al. |
| 6,355,431 | B1 | 3/2002 | Chee et al. |
| 6,361,671 | B1 | 3/2002 | Mathies et al. |
| 6,384,684 | B1 | 5/2002 | Redman-White |
| 6,403,957 | B1 | 6/2002 | Fodor et al. |
| 6,406,848 | B1 | 6/2002 | Bridgham et al. |
| 6,413,792 | B1 | 7/2002 | Sauer et al. |
| 6,429,027 | B1 | 8/2002 | Chee et al. |
| 6,432,360 | B1 | 8/2002 | Church |
| 6,433,386 | B1 | 8/2002 | Yun et al. |
| 6,459,398 | B1 | 10/2002 | Gureshnik et al. |
| 6,465,178 | B2 | 10/2002 | Chappa et al. |
| 6,475,728 | B1 | 11/2002 | Martin et al. |
| 6,482,639 | B2 | 11/2002 | Snow et al. |
| 6,485,944 | B1 | 11/2002 | Church et al. |
| 6,499,499 | B2 | 12/2002 | Dantsker et al. |
| 6,511,803 | B1 | 1/2003 | Church et al. |
| 6,518,024 | B2 | 2/2003 | Choong et al. |
| 6,518,146 | B1 | 2/2003 | Singh et al. |
| 6,535,824 | B1 | 3/2003 | Mansky et al. |
| 6,537,881 | B1 | 3/2003 | Rangarajan et al. |
| 6,538,593 | B2 | 3/2003 | Yang et al. |
| 6,545,620 | B2 | 4/2003 | Groeneweg |
| 6,571,189 | B2 | 5/2003 | Jensen et al. |
| 6,602,702 | B1 | 8/2003 | McDevitt et al. |
| 6,605,428 | B2 | 8/2003 | Klinger et al. |
| 6,613,513 | B1 | 9/2003 | Parce et al. |
| 6,624,637 | B1 | 9/2003 | Pechstein |
| 6,627,154 | B1 | 9/2003 | Goodman et al. |
| 6,654,505 | B2 | 11/2003 | Bridgham et al. |
| 6,682,899 | B2 | 1/2004 | Bryan et al. |
| 6,682,936 | B2 | 1/2004 | Kovacs |
| 6,700,814 | B1 | 3/2004 | Nahas et al. |
| 6,780,591 | B2 | 8/2004 | Williams et al. |
| 6,806,052 | B2 | 10/2004 | Bridgham et al. |
| 6,828,100 | B1 | 12/2004 | Ronaghi |
| 6,831,994 | B2 | 12/2004 | Bridgham et al. |
| 6,859,570 | B2 | 2/2005 | Walt et al. |
| 6,888,194 | B2 | 5/2005 | Yoshino |
| 6,906,524 | B2 | 6/2005 | Chung et al. |
| 6,919,211 | B1 | 7/2005 | Fodor et al. |
| 6,926,865 | B2 | 8/2005 | Howard |
| 6,939,451 | B2 | 9/2005 | Zhao et al. |
| 6,953,958 | B2 | 10/2005 | Baxter et al. |
| 6,969,488 | B2 | 11/2005 | Bridgham et al. |
| 6,998,274 | B2 | 2/2006 | Chee et al. |
| 7,008,550 | B2 | 3/2006 | Li et al. |
| 7,019,305 | B2 | 3/2006 | Eversmann et al. |
| 7,022,288 | B1 | 4/2006 | Boss |
| 7,033,754 | B2 | 4/2006 | Chee et al. |
| 7,037,687 | B2 | 5/2006 | Williams et al. |
| 7,049,645 | B2 * | 5/2006 | Sawada et al. .............. 257/292 |
| 7,060,431 | B2 | 6/2006 | Chee et al. |
| 7,084,641 | B2 | 8/2006 | Brederlow et al. |
| 7,085,502 | B2 | 8/2006 | Shushakob et al. |
| 7,087,387 | B2 | 8/2006 | Gerdes et al. |
| 7,090,975 | B2 | 8/2006 | Shultz et al. |
| 7,097,973 | B1 | 8/2006 | Zenhausern |
| 7,105,300 | B2 | 9/2006 | Parce et al. |
| 7,169,560 | B2 | 1/2007 | Lapidus et al. |
| 7,190,026 | B2 | 3/2007 | Lotfi |
| 7,192,745 | B2 | 3/2007 | Jaeger |
| 7,193,453 | B2 | 3/2007 | Wei et al. |
| 7,211,390 | B2 | 5/2007 | Rothberg |
| 7,223,540 | B2 | 5/2007 | Pourmand et al. |
| 7,226,734 | B2 | 6/2007 | Chee et al. |
| 7,238,323 | B2 | 7/2007 | Knapp et al. |
| 7,244,559 | B2 | 7/2007 | Rothberg et al. |
| 7,244,567 | B2 | 7/2007 | Chen |
| 7,264,929 | B2 | 9/2007 | Rothberg et al. |
| 7,264,934 | B2 | 9/2007 | Fuller |
| 7,265,929 | B2 | 9/2007 | Umeda et al. |
| 7,276,749 | B2 | 10/2007 | Martin et al. |
| 7,282,370 | B2 | 10/2007 | Bridgham et al. |
| 7,291,496 | B2 | 11/2007 | Holm-Kennedy |
| 7,297,518 | B2 | 11/2007 | Quake et al. |
| 7,298,475 | B2 | 11/2007 | Gandhi et al. |
| 7,303,875 | B1 | 12/2007 | Bock et al. |
| 7,317,216 | B2 | 1/2008 | Holm-Kennedy |
| 7,323,305 | B2 | 1/2008 | Leamon et al. |
| 7,335,762 | B2 | 2/2008 | Rothberg et al. |
| 7,359,058 | B2 | 4/2008 | Kranz et al. |
| 7,363,717 | B2 | 4/2008 | Ekseth et al. |
| 7,381,936 | B2 | 6/2008 | Tan et al. |
| 7,394,263 | B2 | 7/2008 | Pechstein et al. |
| 7,419,636 | B2 | 9/2008 | Aker et al. |
| 7,455,971 | B2 | 11/2008 | Chee et al. |
| 7,462,512 | B2 | 12/2008 | Levon et al. |
| 7,465,512 | B2 | 12/2008 | Wright et al. |
| 7,466,258 | B1 | 12/2008 | Akopyan et al. |
| 7,470,352 | B2 | 12/2008 | Eversmann et al. |
| 7,482,153 | B2 | 1/2009 | Okada et al. |
| 7,515,124 | B2 | 4/2009 | Yaguma et al. |
| 7,575,865 | B2 | 8/2009 | Leamon et al. |
| 7,595,883 | B1 | 9/2009 | El Gamal et al. |
| 7,605,650 | B2 | 10/2009 | Forbes |
| 7,608,810 | B2 | 10/2009 | Yamada |
| 7,609,303 | B1 | 10/2009 | Lee |
| 7,612,817 | B2 | 11/2009 | Tay |
| 7,667,501 | B2 | 2/2010 | Surendranath et al. |
| 7,686,929 | B2 | 3/2010 | Toumazou et al. |
| 7,695,907 | B2 | 4/2010 | Miyahara et al. |
| 7,733,401 | B2 | 6/2010 | Takeda |
| 7,785,790 | B1 | 8/2010 | Church et al. |
| 7,859,029 | B2 | 12/2010 | Lee et al. |
| 7,885,490 | B2 | 2/2011 | Heideman et al. |

(56) References Cited

U.S. PATENT DOCUMENTS

| | | |
|---|---|---|
| 7,888,013 B2 | 2/2011 | Miyahara et al. |
| 7,888,708 B2 | 2/2011 | Yazawa et al. |
| 7,923,240 B2 | 4/2011 | Xu |
| 7,932,034 B2 | 4/2011 | Esfandyarpour et al. |
| 7,948,015 B2 | 5/2011 | Rothberg et al. |
| 7,960,776 B2 | 6/2011 | Kim et al. |
| 7,981,362 B2 | 7/2011 | Glezer et al. |
| 8,067,731 B2 | 11/2011 | Matyjaszczyk et al. |
| 8,124,936 B1 | 2/2012 | Lagna |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,343,856 B2 | 1/2013 | Therrien et al. |
| 8,426,898 B2 | 4/2013 | Rothberg et al. |
| 8,449,824 B2 | 5/2013 | Sun |
| 8,552,771 B1 | 10/2013 | Jordan et al. |
| 8,558,288 B2 | 10/2013 | Rothberg et al. |
| 8,592,154 B2 | 11/2013 | Rearick et al. |
| 8,673,627 B2 | 3/2014 | Nobile et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | William et al. |
| 2002/0150909 A1 | 10/2002 | Stuelpnagel et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 | 3/2003 | Matson |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0124572 A1 | 7/2003 | Umek et al. |
| 2003/0124599 A1 | 7/2003 | Chen et al. |
| 2003/0138809 A1 | 7/2003 | Williams et al. |
| 2003/0141928 A1 | 7/2003 | Lee |
| 2003/0141929 A1 | 7/2003 | Casper et al. |
| 2003/0148301 A1 | 8/2003 | Aono et al. |
| 2003/0148344 A1 | 8/2003 | Rothberg et al. |
| 2003/0155942 A1 | 8/2003 | Thewes et al. |
| 2003/0157504 A1 | 8/2003 | Chee et al. |
| 2003/0186262 A1 | 10/2003 | Cailloux et al. |
| 2003/0194740 A1 | 10/2003 | Williams |
| 2003/0211502 A1 | 11/2003 | Sauer et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0079636 A1 | 4/2004 | Hsia et al. |
| 2004/0106211 A1 | 6/2004 | Kauer et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0202582 A1 | 9/2005 | Eversmann et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2006/0000772 A1 | 1/2006 | Sano et al. |
| 2006/0016699 A1 | 1/2006 | Kamahori et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber et al. |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0099208 A1 | 5/2007 | Drmanac et al. |

(56) References Cited

U.S. PATENT DOCUMENTS

| | | |
|---|---|---|
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0035494 A1 | 2/2008 | Gomez et al. |
| 2008/0094074 A1 | 4/2008 | Kim et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0185616 A1 | 8/2008 | Johnson et al. |
| 2008/0186093 A1 | 8/2008 | Forbes |
| 2008/0197022 A1 | 8/2008 | Suzuki et al. |
| 2008/0210931 A1 | 9/2008 | Truong et al. |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1* | 1/2009 | Rothberg et al. ............ 204/556 |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0120905 A1 | 5/2009 | Kohl et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0316477 A1 | 12/2009 | Horiuchi |
| 2010/0007326 A1 | 1/2010 | Nakazato |
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1* | 9/2011 | Sawada et al. ............ 422/82.01 |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1* | 12/2011 | Parris et al. ............ 365/185.18 |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0001779 A1 | 1/2012 | Fife et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0074956 A1 | 3/2012 | Fife et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0161207 A1 | 6/2012 | Homyk et al. |
| 2012/0168307 A1 | 7/2012 | Fife |
| 2012/0173159 A1 | 7/2012 | Davey et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| DE | 102008012899 | 9/2009 |
| EP | 1975246 | 3/1984 |
| EP | 0223618 | 5/1987 |
| EP | 1371974 | 12/2003 |
| EP | 1432818 | 6/2004 |
| EP | 1542009 | 6/2005 |
| EP | 1557884 | 7/2005 |
| EP | 1870703 | 12/2007 |
| EP | 2307577 | 4/2011 |
| GB | 2457851 | 9/2009 |
| GB | 2461127 B | 7/2010 |
| JP | 58070155 | 4/1983 |
| JP | 2000055874 | 2/2000 |
| JP | 2002272463 | 9/2002 |
| JP | 2005218310 | 8/2004 |
| JP | 05077210 | 3/2005 |
| JP | 2005-518541 | 6/2005 |
| JP | 05518541 | 6/2005 |
| JP | 06138846 | 6/2006 |

(56) References Cited

FOREIGN PATENT DOCUMENTS

| JP | WO 2009081890 | * | 7/2009 |
|---|---|---|---|
| JP | 2011-525810 | | 9/2011 |
| KR | 10-0442838 | | 7/2004 |
| KR | 10-0455283 | | 10/2004 |
| WO | WO 89/09283 | | 10/1989 |
| WO | WO 98/13523 | | 4/1998 |
| WO | WO 98/46797 | | 10/1998 |
| WO | WO 01/20039 | | 3/2001 |
| WO | WO 01/42498 | | 6/2001 |
| WO | WO 01/81896 | | 11/2001 |
| WO | WO 02/077287 | | 10/2002 |
| WO | WO 02/086162 | | 10/2002 |
| WO | WO 03/073088 | | 9/2003 |
| WO | WO 2004/040291 | | 5/2004 |
| WO | WO 2004040291 | | 5/2004 |
| WO | WO 2004048962 | | 6/2004 |
| WO | WO 2005015156 | | 2/2005 |
| WO | WO 2005/047878 | | 5/2005 |
| WO | WO 2005043160 | | 5/2005 |
| WO | WO 2005/054431 | | 6/2005 |
| WO | WO 2005602049 | | 7/2005 |
| WO | WO 2005/084367 | | 9/2005 |
| WO | WO 2005090961 | | 9/2005 |
| WO | WO 2006/005967 | | 1/2006 |
| WO | WO 2006/022370 | | 3/2006 |
| WO | WO 2007002204 | | 1/2007 |
| WO | WO 2007/086935 | | 8/2007 |
| WO | WO-2008/007716 | | 1/2008 |
| WO | WO 2008/058282 | | 5/2008 |
| WO | WO 2008/076406 | | 6/2008 |
| WO | WO 2008/107014 | | 9/2008 |
| WO | WO 2009/012112 | | 1/2009 |
| WO | WO 2009041917 | | 4/2009 |
| WO | WO 2009074926 | | 6/2009 |
| WO | 2009/158006 | | 12/2009 |
| WO | WO 2009/158006 | | 12/2009 |
| WO | WO 2010/008480 | | 1/2010 |
| WO | WO 2010/047804 | | 4/2010 |
| WO | WO 2010/047804 A8 | | 4/2010 |
| WO | WO 2010/138182 | | 12/2010 |
| WO | WO 2010/138188 | | 12/2010 |
| WO | WO 2012/003359 | | 1/2012 |
| WO | WO 2012/003363 | | 1/2012 |
| WO | WO 2012/003368 | | 1/2012 |
| WO | WO 2012/003380 | | 1/2012 |
| WO | WO 2012/006222 | | 1/2012 |

OTHER PUBLICATIONS

Ahmadian, A. et al., "Single-nucleotide polymorphism analysis by pyrosequencing", *Anal. Biochem*, vol. 280, 2000, pp. 103-110.
Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.
AU2011226767, , "Search Information Statement", Oct. 26, 2011, pp. 1-3.
Bandiera, L et al., "A fully electronic sensor for the measurement of cDNA hybridization kinetics", *Biosens Bioelectron*, vol. 22, 2007, pp. 2108-2114.
Barbaro, M et al., "A Charge-Modulated FET for Detection of Biomolecular Processes: Conception, Modeling, and Simulation", *IEEE Transactions on Electron Devices*, vol. 53(1), 2006, pp. 158-166.
Barbaro, M et al., "A CMOS, Fully Integrated Sensor for Electronic Detection of DNA Hybridization", *IEEE Electron Device Letters*, vol. 27(7), 2006, pp. 595-597.
Barbaro, M et al., "Fully electronic DNA hybridization detection by a standard CMOS biochip", *Sensors and Actuators B Chemical*, vol. 118, 2006, pp. 41-46.
Bashford, G et al., "Automated bead-trapping apparatus and control system for single-molecule DNA sequencing", *Optics Express*, vol. 16(5), Mar. 3, 2008, pp. 3445-3455.

Baumann, W et al., "Microelectronic sensor system for microphysiological application on living cells", *Sensors Actuators B*, vol. 55, 1999, pp. 77-89.
Bausells, J et al., "Ion-sensitive field-effect transistors fabricated in a commercial CMOS technology", *Sensors and Actuators B Chemical*, vol. 57, 1999, pp. 56-62.
Bergveld, P., "ISFET, Theory and Practice", *IEEE Sensor Conference*, Toronto, Oct. 2003, pp. 1-26.
Bergveld, P., "Thirty years of ISFETOLOGY What happened in the past 30 years and what may happen in the next 30 years", *Sensors and Actuators B*, vol. 88, vol. 88, 2003, pp. 1-20.
Besselink, G et al., "ISFET Affinity Sensor", *Methods in Biotechnology*, vol. 7: *Affinity Biosensors: Techniques and Protocols*, 1998, pp. 173-185.
Bobrov, P. et al., "Chemical sensitivity of an ISFET with Ta2O5 membrane in strong acid and alkaline solutions", *Sensors and Actuators B*, vol. 3, 1991, pp. 75-81.
Bousse, L et al., "A process for the combined fabrication of ion sensors and CMOS circuits", *IEEE Electron Device Letters*, vol. 9(1), Jan. 1988, pp. 44-46.
Bousse, L et al., "Zeta potential measurements of Ta2O5 and SiO2 thin films", *J. Colloid Interface Sci.*, vol. 147(1), Nov. 1991, pp. 22-32.
Chen, et al., "Nanoscale field effect transistor for biomolecular signal amplification", *App Phys Letter*, vol. 91, 2007, pp. 243511-1-243511-3.
Chen, et al., "Silicone-based nanoelectronic field-effect pH sensor with local gate control", *App Phys Letter*, vol. 89, 2006, pp. 223512-1-223512-3.
Chou, J. et al., "Letter to the Editor on Simulation of Ta2O5 gate ISFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-61.
Chung, W-Y et al., "ISFET interface circuit embedded with noise rejection capability", *Electronics Letters*, vol. 40(18), e-pub ; 2 pages, 2004.
Chung, W-Y et al., "ISFET performance enhancement by using the improved circuit techniques", *Sensors and Actuators B*, vol. 113, 2006, pp. 555-562.
Eijkel, J. et al., "Measuring Donnan-related phenomena using a solid-state ion sensor and a concentration-step method", *J. Membrane Sci.*, vol. 127, 1997, pp. 203-221.
Eijkel, J. , "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.
Eriksson, J et al., "Pyrosequencing technology at elevated temperature", *Electrophoresis*, vol. 25, 2004, pp. 20-27.
Esfandyarpour, H. et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128 x 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . . ", 17.3.2 *Chemfet Sensors*, 1996, pp. 499-501.
Fritz, et al., "Electronic detection of DNA by its intrinsic molecular charge", *PNAS*, vol. 99(22), 2002, pp. 14142-14146.
GB0811656.8 Search and Examination Report Mailed Mar. 12, 2010.

(56) References Cited

OTHER PUBLICATIONS

GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", *Proc IEEE 1992 Intl Conf Microelec Test Struct*, vol. 5, 1992, pp. 156-159.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P et al., "Design of a Single-Chip pH Sensor Using a Conventional 0.6—μm CMOS Process", *IEEE Sensors Journal*, vol. 4(6), 2004, pp. 706-712.
Hammond, P et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hampster ovary cell line using Illumina sequencing technology", *BMC Genomics*, 12:67, 2011, pp. 1-8.
Han, Y., "Label-free detection of biomolecules by a field-effect transistor microarray biosensor with bio-functionalized gate surfaces", Masters Dissertation, 2006, pp. 1-63.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hijikata, M. et al., "Identification of a Single Nucleotide Polymorphism in the MXA Gene Promoter (T/T at nt -88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al., "32 x 32 pH Image Sensors for Real Time Observation of Biochemical Phenomena", *Transducers & Eurosensors'07*, 14th International Conference on Solid-State, Actuators and Microsystems, Lyon, France, Jun. 10-14, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360.
Ji, H. et al., "Contact Imaging: Simulation and Experiment", *IEEE Trans Circuits Systems—I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), Jul. 30, 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer",*Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J et al., "A Massively Parallel PicoTiterPlate Based Platform for Discrete Picoliter-Scale Polymerase Chain Reactions", *Electrophoresis*, vol. 24, Nov 24, 2003, pp. 3769-3777.
Leamon, J. et al., "Cramming More Sequencing Reactions onto Microreactor Chips", *Chemical Reviews*, 107:, 2007, 3367-3376.
Li, et al., "Sequence-Specific Label-Free DNA Sensors Based on Silico Nanowires", *Nano Letters,*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Prooceedings of the 1996 IEEE International Conference on Microelectronic Test Structures*, vol. 9, 1996, pp. 123-128.
Margulies, M. et al., "Genome sequencing in microfabricated high-density picolitre reactors", *Nature*, vol. 437, 2005, pp. 376-380.
Marshall, A. et al., "DNA chips: an array of possibilities", *Nature Biotechnology*, vol. 16, Jan. 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J*, vol. 3(3), 2003, pp. 317-325.
Meyburg, S. et al., "N-Channel field-effect transistors with floating gates for extracellular recordings", *Biosens Bioelectron*, vol. 21(7), Jan. 15, 2006, pp. 1037-1044.
Milgrew, M et al., "A large transistor based sensor array chip for direct extracellular imaging", *Sensors and Actuators B Chemical*, vol. 111-112, 2005, pp. 347-353.
Milgrew, M. et al., "Microsensor Array Technology for Direct Extracellular Imaging", Apr. 5, 2006, pp. 1-23.
Milgrew, M et al., "The development of scalable sensor arrays using standard CMOS technology", *Sensors and Actuators B*, 103, 2004, pp. 37-42.
Milgrew, M et al., "The fabrication of scalable multi-sensor arrays using standard CMOS technology", *2003 IEEE Custom Integrated Circuits Conference*, 2003, pp. 513-516.
Milgrew, M. et al., "A 16 x 16 CMOS proton camera array for direct extracellular imaging of hydrogen-ion activity", IEEE Intl Solid-State Circuits Conf, Session 32:24, 2008, pp. 590-591; 638.
Milgrew, M. et al., "Matching the transconductance characteristics of CMOS ESFET arrays by removing trapped charge", *IEEE Trans Electron Devices*, vol. 55(4), 2008, pp. 1074-1079.
Miyahara, Y et al., "Direct Transduction of Primer Extension into Electrical Signal Using Genetic Field Effect Transistor", *Micro Total Analysis Systems 2004*, vol. 1, Proceedings of uTAS 2004, 8th International Conference on Miniaturized Systems for Chemistry and Life Sciences, Malmo, Sweden, Sep. 26-30, 2004, pp. 303-305.
Miyahara, Y. et al., "Biochip Using Micromatchining Technology", *J. Institute of Electrostatics, Japan*, vol. 27(6), 2003, pp. 268-272.
Miyahara, Y. et al., "Potentiometric Detection of DNA Molecules Using Field Effect Transistor", *The Japan Society of Applied Physics*, No. 3 (Translation included), 2003, pp. 1180, 30A-S2.
Nyren, P. et al., "Enzymatic Method for Continuous Monitoring of Inorganic Pyrophosphate Synthesis", *Analytical Biochemistry*, vol. 151, 1985, 504-509.
Oelbner, W. et al., "Encapsulation of ESFET sensor chips", *Sensors Actuators B*, vol. 105, 2005, pp. 104-117.
Oelbner, W. et al., "Investigation of the dynamic response behaviour of ISFET pH sensors by means of laser Doppler velocimetry (LDV)", *Sensors Actuators B*, vol. 26-27, 1995, pp. 345-348.
Offenhausser, A. et al., "Field-Effect transistor array for monitoring electrical activity from mammalian neurons in culture", *Biosensors & Bioelectronics*, vol. 12(8), 1997, pp. 819-826.
Patolsky, F. et al., "Nanowire-Based Biosensors", *Analyt Chem 1*, vol. 78(13), Jul. 1, 2006, pp. 4261-4269.
PCT/JP2005/001987 International Search Report Mailed Apr. 5, 2005.
PCT/JP2005/015522 International Search Report (includes English translation) Mailed Sep. 27, 2005,.
PCT/US/2009/05745 International Preliminary Report on Patentability.
PCT/US/2009/05745 International Search Report.
PCT/US/2009/05745 Written Opinion.
PCT/US2007/025721 Declaration of Non-Establishment of International Search Report Mailed Jul. 15, 2008.
PCT/US2007/025721 International Prelimary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion.

(56) References Cited

OTHER PUBLICATIONS

PCT/US2010/001543 International Preliminary Report on Patentability Mailed Nov. 29, 2011, pp. 1-8.
PCT/US2010/001543 International Search Report and Written Opinion Oct. 13, 2010, pp. 1-12.
PCT/US2010/001553 International Search Report Mailed Jul. 28, 2010, pp. 1-2.
PCT/US2010/001553 International Preliminary Report on Patentability Mailed Dec. 8, 2011, pp. 1-10.
PCT/US2010/001553 Written Opinion Mailed Jul. 14, 2010, pp. 1-6.
PCT/US2010/48835 International Search Report and Written Opinion Mailed 12/16/10, pp. 1-12.
PCT/US2011/042655 International Search Report Mailed Oct. 21, 2011, pp. 1-2.
PCT/US2011/042660 International Search Report Mailed Nov. 2, 2011.
PCT/US2011/42669 International Search Report Mailed Jan. 9, 2012, pp. 1-5.
PCT/US2011/42669 Written Opinion Mailed Jan. 9, 2012, pp. 1-5.
PCT/US2011/42683 International Search Report Mailed Feb. 16, 2012.
PCT/US2011/42683 Written Opinon Mailed Feb. 16, 2012.
Poghossian, A. et al., "Functional testing and characterization of ISFETs on wafer level by means of a micro-droplet cell", *Sensors*, vol. 6, 2006, pp. 397-404.
Pourmand, N et al., "Direct electrical detection of DNA synthesis", *PNAS*, vol. 103(17), 2006, pp. 6466-6470.
Pouthas, F. et al., "Spatially resolved electronic detection of biopolymers", *Phys Rev*, vol. 70, 2004, pp. 031906-1-031906-8.
Premanode, B. et al., "A composite ISFED readout circuit employing current feedback", *Sensors Actuators B*, vol. 127, 2007, pp. 486-490.
Premanode, B. et al., "A novel, low power biosensor for real time monitoring of creatine and urea in peritoneal dialysis", *Sensors Actuators B*, vol. 120, 2007, pp. 732-735.
Premanode, B. et al., "Ultra-low power precision ISFET readout using global current feedback", *Electronic Lett*, vol. 42(22), Oct. 26, 2006, 2 pages.
Purushothaman, S et al., "Towards Fast Solid State DNA Sequencing", *IEEE ISCAS 2002 Proceedings*, 2002, pp. IV-169-IV-172.
Purushothaman, S. et al., "Protons and single nucleotide polymorphism detection: A simple use for the Ion Sensitive Field Effect Transistor", *Sensors and Actuators B Chemical*, vol. 114, 2006, pp. 964-968.
Rodriguez-Villegas, E., "Solution to trapped charge in FGMOS transistors, vol. 39(19)", *Electronics Letters*, 2003.
Ronaghi, M. et al., "A Sequencing Method Based on Real-Time Pyrophosphate", *Science*, vol. 281, Jul. 17, 1998, pp. 363-365.
Sakata, T. et al., "Cell-based field effect devices fo cell adhesion analysis", *International Conference on Microtechnologies in Medicine and Biology*, May 9-12, 2006, Okinawa, Japan, 2006, pp. 177-179.
Sakata, T. et al., "Detection of DNA recognition events using multi-well field effect transistor", *Biosensors and Bioelectronics* vol. 21, 2005, pp. 827-832.
Sakata, T. et al., "Detection sensitivity of genetic field effect transistor combined with charged nanoparticle-DNA conjugate", *Proceedings of 2006 International Conference on Microtechnologies in Medicine and Biology*, May 9-12, 2005, Okinawa, Japan, 2006, pp. 97-100.
Sakata, T. et al., "Direct detection of single nucleotide polymorphism using genetic field effect transistor", *Digest of Papers Microprocesses and Nanotechnology* 2004, Osaka, Japan, 2004 International Microprocesses and Nanotechnology Conference, 2004, pp. 226-227.
Sakata, T. et al., "Direct Detection of Single-Base Extension Reaction Using Genetic Field Effect Transistor", *Proceedings of 3rd Annual International IEEE EMBS Special Topic Conference on Microtechnologies in Medicine and Biology*, Kahuku, Oahu, HI, May 12-15, 2005, 2005, pp. 219-222.
Sakata, T. et al., "Direct transduction of allele-specific primer extension into electrical signal using genetic field effet transistor", *Biosensors and Bioelectonics* vol. 22, 2007, pp. 1311-1316.
Sakata, T. et al., "DNA Analysis Chip Based on Field-Effect Transistors", *Japanese Journal of Applied Physics*, vol. 44, No. 4B, 2005, 2005, pp. 2854-2859.
Sakata, T. et al., "DNA Sequencing Based on Intrinsic Molecular Charges", *Angewandte Chemie International Edition*, 2006, vol. 45, 2006, pp. 2225-2228.
Sakata, T. et al., "DNA Sequencing Based on Intrinsic Molecular Charges", *Angewandte Chemie International Edition*, 2006, vol. 118, 2006, pp. 2283-2286.
Sakata, T. et al., "DNA Sequencing Using Genetic Field Effect Transistor", *13th International Conference on Solid-State Sensors, Actuators and Microsystems*, Jun. 5-9, 2005, Seoul, Korea, 2005, pp. 1676-1679.
Sakata, T. et al., "Immobilization of oligonucleotide probes on Si3N4 surface and its application to genetic field effect transistor", *Materials Science and Engineering: C*, vol. 24, 2004, pp. 827-832.
Sakata, T. et al., "Potential Behavior of Biochemically Modified Gold Electrode for Extended-Gate Field-Effect Transistor", *Japanese Journal of Applied Physics*, vol. 44, No. 4B, 2005, 2005, pp. 2860-2863.
Sakata, T. et al., "Potential Response of Genetic Field Effect Transistor to Charged Nanoparticle-DNA Conjugate", *Digest of Papers Microprocesses and Nanotechnology* 2005, Tokyo, Japan, 2005 Intl Microprocesses and Nanotech Conference, Hotel Bellclassic, 2005, pp. 42-43.
Sakata, T. et al., "Potentiometric Detection of Allele Specific Oligonucleotide Hybridization Using Genetic Field Effect Transistor", *Micro Total Anslysis Systems* 2004, vol. 1, 8th International Conference on Miniaturized Systems for Chemistry and Life Sciences, Sep. 26-30, 2004, Malmo, Sweden, 2004, pp. 300-302.
Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston Massachusetts, 2004, pp. 393-398.
Sakata, T. et al., "Potentiometric Detection of DNA Using Genetic Transistor", *Denki Gakkai Kenkyukai Shiryo Chemical Sensor Kenkyukai*, CHS-03-51-55, 2003, pp. 1-5.
Sakata, T. et al., "Potentiometric Detection of Single Nucleotide Polymorphism by Using a Genetic Field-effect transistor", *ChemBioChem* 2005, vol. 6, 2005, pp. 703-710.
Sakurai, T. et al., "Real-Time Monitoring of DNA Polymerase Reactions by a Micro ISFET pH Sensor", *Anal Chem*, vol. 64(17), 1992, pp. 1996-1997.
Salama, K., "CMOS luminescence detection lab-on-chip: modeling, design, and characterization", *Thesis*, Presented at Stanford University, 2005, pp. ii-78.
Salama, K., "Modeling and simulation of luminescence detection platforms", *Biosensors & Bioelectronics*, 2004, 1377-1386.
Sawada, K. et al., "A novel fused sensor for photo- and ion-sensing", *Sensors Actuators B*, vol. 106, 2005, pp. 614-618.
Sawada, K. et al., "Highly sensitive ion sensors using charge transfer technique", *Sensors Actuators B*, vol. 98, 2004, pp. 69-72.
Schasfoort, et al., "Field-effect flow control for microfabricated fluidic networks", *Science*, vol. 286(5441), Oct. 29, 1999, pp. 942-945.
Schasfoort, B. et al., "A new approach to immunoFET operation" *Biosensors & Bioelectronics*, vol. 5, 1990, pp. 103-124.
Schoning, M. et al., "Bio FEDs (Field-Effect Devices): State-of-the-Art and New Directions", *Electroanalysis*, vol. 18(19-20), 2006, pp. 1893-1900.
SG200903992-6 Search and Examination Report (Favourable) Mailed Jan. 20, 2011.
Shah, N., "Microfabrication of a parellel-array DNA pyrosequencing chip", *NNIN REU Research Accomplishments*, 2005, pp. 130-131.
Shepherd, L. et al., "A biochemical translinear principle with weak inversion ISFETs", *IEEE Trans Circuits Syst—I*, vol. 52(12), Dec. 2005, pp. 2614-2619.
Shepherd, L. et al., "A novel voltage-clamped CMOS ISFET sensor interface", *IEEE*, 2007, pp. 3331-3334.

(56) References Cited

OTHER PUBLICATIONS

Shepherd, L. et al., "Towards direct biochemical analysis with weak inversion ISFETS", *Intl Workshop on Biomedical. . .*, 2004, S1.5-5-S1.5-8.
Shepherd, L. et al., "Weak inversion ISFETs for ultra-low power biochemical sensing and real-time analysis", *Sensors Actuators B*, vol. 107, 2005, pp. 468-473.
Shi, Y. et al., "Radical Capillary Array Electrophoresis Microplace and Scanner for High-Performance Nucleic Acid Analysis", *Anal. Chem.*, vol. 71(23), 1999, pp. 5354-5361.
Simonian, et al., "FET bases biosensors for the direct detection of organophosphate neurotoxins", *Electroanalysis*, vol. 16(22), 2004, pp. 1896-1906.
Souteyrand, E. et al., "Direct detection of the hybridization of synthetic homo-oligomer DNA sequences by field effect", *J Phys Chem B*, vol. 101(15), 1997, pp. 2980-2985.
Takenaka, S. et al., "DNA Sensing on a DNA Probe-Modified Electrode Using Ferrocenylnaphthalene Dimide as the Electrochemically Active Ligand", *Anal. Chem.*, vol. 72(6), 2000, pp. 1334-1341.
Tomaszewski, D. et al., "Electrical characterization of ISFETs", *J Telecomm Info Technol*, Mar. 2007, pp. 55-60.
Toumazou, C. et al., "Using transistors to linearase biochemistry", *Electronics Letters*, vol. 43(2), Jan. 18, 2007, 3 pages.
Truman, P., "Monitoring liquid transport and chemical composition in lab on . . . ", *Lab on a Chip*, vol. 6, 2006, pp. 1220-1228.
Uslu, F. et al., "Labelfree fully electronic nucleic acid detection system based on a field-effect transistor device", *Biosens & Bioelectron*, vol. 19(12), 2004, pp. 1723-1731.
Van Der Wouden, E. et al., "Directional flow induced by synchronized longitudinal and zeta-potential controlling AC-electrical fields", *Lab Chip*, vol. 6(10), 2006, pp. 1300-1305.
Van Hal, R.E.G. et al., "A general model to describe the electrostatic potential at electrolyte oxide interfaces", *Advances in Colloid and Interface Science*, vol. 69, 1996, pp. 31-62.
Van Kerkhof, J et al., "The ISFET based heparin sensor with a monolayer of protamine as affinity ligand", *Biosensors & Bioelectronics*, vol. 10(3), 1995, pp. 269-282.
Van Kerkhof, J. et al., "ISFET Responses on a stepwise change in electrolyte concentration at constant pH", *Sensors Actuators B: Chemical*, vol. 18-19, Mar. 1994, pp. 56-59.
Van Kerkhof, J., "The Development of an ISFET-based Heparin Sensor", *Thesis*, 1994.
Wagner, T et al., "All-in-one" solid-state device based on a light-addressable potentiometric sensor platform, *Sensors and Actuators B*, vol. 117, 2006, pp. 472-479.
Woias, P , "Modelling the short time response of ISFET sensors", *Sensors and Actuators B*, vol. 24-25, 1995, pp. 211-217.
Woias, P. et al., "Slow pH response effects of silicon nitride ISFET sensors", *Sensors and Actuators B*, vol. 48, 1998, pp. 501-504.
Wu, P. et al., "DNA and protein microarray printing on silicon nitride waveguide surfaces", *Biosensens Bioelectron*, vol. 21(7), 2006, pp. 1252-1263.
Xu, J-J et al., "Analytical Aspects of FET-Based Biosensors", *Frontiers in Bioscience*, Oct. 2005, pp. 420-430.
Yeow, T.C.W., "A very large integrated pH-ISFET sensor array chip compatible with standard CMOS processes", *Sensor and Actuators B*, vol. 44, 1997, pp. 434-440.
Yuqing, M. et al., "Ion sensitive field effect trnasducer-based biosensors", *Biotechnology Advances*, vol. 21, 2003, 527-534.
Zhang, X et al., "32-Channel Full Customized CMOS Biosensor Chip for Extracellular neural Signal Recording", *Proceedings of the 2nd International IEEE EMBs Conference on Neural Engineering*, Arlington, VA—, 2005, pp. v-viii.
Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.
Hideshima, S. et al., "Detection of tumor marker in blood serum using antibody-modified field effect ransistor with optimized BSA blocking", *Sensors and Actuations B: Chemical*, vol. 161, 2012, pp. 146-150.
Lee, C-S et al., "Ion-sensitive Field-Effect Transistor for Biological Sensing", *Sensors*, vol. 9, 2009, pp. 7111-7131.
Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.
Starodub, N. et al., "Immunosensor for the determination of the herbicide simazine based on an ion-selective field-effect transistor", *Analytica Chimica Acta*, vol. 424, 2000, pp. 37-43.
Wang, W. et al., "Label-free detection of small-molecule-protein interactions by using nanowire nanosensors", *Proceedings of the National Academy of Sciences (PNAS)*, vol. 102,(9), 2005, pp. 3208-3212.
PCT/US2011/042665 International Search Report Mailed Nov. 2, 2011.
PCT/US2011/042668 International Search Report Mailed Oct. 28, 2011.
PCT/JP2005/015522 International Search Report Mailed Sep. 27, 2005.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chinese Patent Application 200780051353.2 Second Office Action Mailed Mar. 5, 2013.
Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
Krause, M. et al., "Extended Gate Electrode Arrays for Extracellular Signal Recordings", Sensors and Actuators B, vol. 70, 2000, pp. 101-107.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
PCT/US2010/048835 International Preliminary Report on Patentability Mailed Mar. 19, 2013.
PCT/US2011/042668 International Preliminary Report on Patentability Mailed Mar. 26, 2013.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.
Pollack, J. et al. "Genome-Wide Analysis of DNA copy-number changes using cDNA Microarrays", Nature Genetics, vol. 23, 1999, pp. 41-46.
EP09798251.6 Extended European Search Report dated Aug. 27, 2013.
EP13161312.7 Extended European Search Report dated Oct. 15, 2013.
EP13163995.7 First Office Action dated Aug. 30, 2013.
EP13164768.7 Extended European Search Report dated Aug. 20, 2013.
EP13164768.7 First Office Action dated Aug. 30, 2013.
Hanshaw, R. et al., "An indicator displacement system for fluorescent detection of phosphate oxyanions under physiological conditions" Science Direct, Tetrahedron Ltrs., vol. 45, 2004, pp. 8721-8724.
JP20120246413 First Office Action dated Jun. 28, 2013.
Maki, W et al., "Nanowire-transistor based ultra-sensitive DNA methylation detection", Biosensors & Bioelectronics, vol. 23, 2008, pp. 780-787.
PCT/US2013/022129 International Search Report and Written Opinion dated Aug. 9, 2013.

(56) References Cited

OTHER PUBLICATIONS

Rothberg, J. et al., "An integrated semiconductor device enabling non-optical genome sequencing" Nature, vol. 475, No. 7356, 2011, pp. 348-352.
Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP11801437.2 Extended European Search Report dated Jul. 25, 2013.
EP11804218.3 Extended European Search Report dated Jul. 11, 2013.
EP11804218.3 First Office Action dated Jul. 29, 2013.
EP11827128.7 European Search Report dated Aug. 1, 2013.
EP13163995.7 Extended European Search Report dated Aug. 20, 2013.
Eriksson, J. et al. "Pyrosequencing Technology at Elevated Temperature" Electrophoresis, vol. 25, 2004, pp. 20-27.
Hizawa, et al. "Sensing Characteristics of Charge Transfer Type pH Sensor by Accumulative Operation" IEEE Sensors, EXCO, Daegu, Korea, 2006, pp. 144-147.
Lee, S. et al. "An Enhanced Glucose Biosensor Using Charge Transfer Techniques" Biosensors and Bioelectronics, vol. 24, 2008, pp. 650-656.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-255.
Milgrew, M.J. et al., "The Development of Scalable Sensor Arrays Using Standard CMOS Technology" ScienceDirect, Sensors and Actuators, vol. 103, 2004, pp. 37-42.
PCT/US2011/042683 International Preliminary Report on Patentability Mailed Jun. 4, 2013.
Premanode, B. et al. "Drift Reduction in Ion-Sensitive FETs Using Correlated Double Sampling", Electronics Letters, IEEE Stevenage, GB, vol. 43 (16) Aug. 2, 2007.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
Bockelmann, U. et al., "Detecting DNA by field effect transistor arrays", *Proceedings of the 2006 IFIP International Conference on Very Large Scale Integration*, 2006, 164-168.
EP13177590.0 EP Search Report Nov. 20, 2013.
EP13177039.8 EP Search Report Nov. 21, 2013.
EP13174555.6 EP Search Report Nov. 21, 2013.
EP13174555.6 EP Extended Search Report Dec. 12, 2013.
EP11801439.8 EP Extended Search Report dated Mar. 7, 2014.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Tokuda, T. et al., "A CMOS image sensor with optical and potential dual imaging function for on-chip bioscientific applications", *Sensors and Actuators A*, vol. 125, No. 2, 2006, 273-280.
Wood, et al. "Base composition-independent hybridization in tetramethylammonium chloride: a method for oligonucleotide screening of highly complex gene libraries" Proc. Nat. Acad. Sci., 1985, pp. 1585-1588.

\* cited by examiner

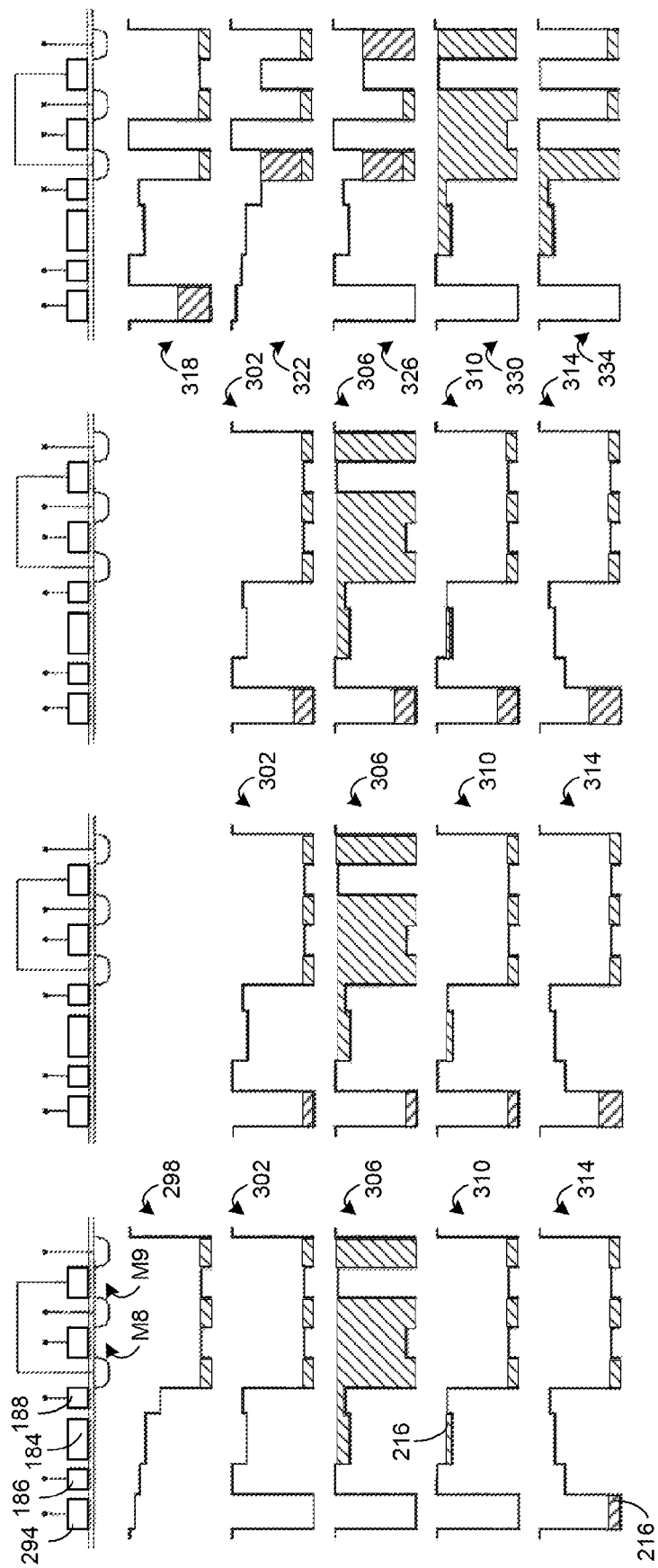

ION-SENSING CHARGE-ACCUMULATION CIRCUITS AND METHODS

RELATED APPLICATIONS

This application claims priority to U.S. Provisional Patent Application Nos. 61/360,493, filed on Jun. 30, 2010; 61/360,495, filed on Jul. 1, 2010; and 61/361,403, filed on Jul. 3, 2010; each of which is herein incorporated by reference in its entirety.

BACKGROUND

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as an "ISFET" (or pHFET). ISFETs conventionally have been explored, primarily in the academic and research community, to facilitate measurement of the hydrogen ion concentration of a solution (commonly denoted as "pH"). The chemically-sensitive sensor referred to herein may be implemented using an ISFET, phFET, chemFet or some other transistor device capable of performing a similar function.

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20 ("Bergveld"), which publication is hereby incorporated herein by reference in its entirety.

Details of fabricating an ISFET using a conventional CMOS (Complementary Metal Oxide Semiconductor) process may be found in Rothberg, et al., U.S. Patent Publication No. 2010/0301398, Rothberg, et al., U.S. Patent Publication No. 2010/0282617, and Rothberg et al, U.S. Patent Publication 2009/0026082; these patent publications are collectively referred to as "Rothberg", and are all incorporated herein by reference in their entirety. In addition to CMOS, however, biCMOS (i.e., bipolar and CMOS) processing may also be used, such as a process that would include a PMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies.

Taking a CMOS example, a P-type ISFET fabrication is based on a p-type silicon substrate, in which an n-type well forming a transistor "body" is formed. Highly doped p-type (p+) regions S and D, constituting a source and a drain of the ISFET, are formed within the n-type well. A highly doped n-type (n+) region B may also be formed within the n-type well to provide a conductive body (or "bulk") connection to the n-type well. An oxide layer may be disposed above the source, drain and body connection regions, through which openings are made to provide electrical connections (via electrical conductors) to these regions. A polysilicon gate may be formed above the oxide layer at a location above a region of the n-type well, between the source and the drain. Because it is disposed between the polysilicon gate and the transistor body (i.e., the n-type well), the oxide layer often is referred to as the "gate oxide."

Like a MOSFET, the operation of an ISFET is based on the modulation of charge concentration (and thus channel conductance) caused by a MOS (Metal-Oxide-Semiconductor) capacitance. This capacitance is constituted by a polysilicon gate, a gate oxide and a region of the well (e.g., n-type well) between the source and the drain. When a negative voltage is applied across the gate and source regions, a channel is created at the interface of the region and the gate oxide by depleting this area of electrons. For an n-well, the channel would be a p-channel (and vice-versa). In the case of an n-well, the p-channel would extend between the source and the drain, and electric current is conducted through the p-channel when the gate-source potential is negative enough to attract holes from the source into the channel. The gate-source potential at which the channel begins to conduct current is referred to as the transistor's threshold voltage VTH (the transistor conducts when VGS has an absolute value greater than the threshold voltage VTH). The source is so named because it is the source of the charge carriers (holes for a p-channel) that flow through the channel; similarly, the drain is where the charge carriers leave the channel.

As described in Rothberg, an ISFET may be fabricated with a floating gate structure, formed by coupling a polysilicon gate to multiple metal layers disposed within one or more additional oxide layers disposed above the gate oxide. The floating gate structure is so named because it is electrically isolated from other conductors associated with the ISFET; namely, it is sandwiched between the gate oxide and a passivation layer that is disposed over a metal layer (e.g., top metal layer) of the floating gage.

As further described in Rothberg, the ISFET passivation layer constitutes an ion-sensitive membrane that gives rise to the ion-sensitivity of the device. The presence of analytes such as ions in an analyte solution (i.e., a solution containing analytes (including ions) of interest or being tested for the presence of analytes of interest), in contact with the passivation layer, particularly in a sensitive area that may lie above the floating gate structure, alters the electrical characteristics of the ISFET so as to modulate a current flowing through the channel between the source and the drain of the ISFET. The passivation layer may comprise any one of a variety of different materials to facilitate sensitivity to particular ions; for example, passivation layers comprising silicon nitride or silicon on/nitride, as well as metal oxides such as silicon, aluminum or tantalum oxides, generally provide sensitivity to hydrogen ion concentration (pH) in an analyte solution, whereas passivation layers comprising polyvinyl chloride containing valinomycin provide sensitivity to potassium ion concentration in an analyte solution. Materials suitable for passivation layers and sensitive to other ions such as sodium, silver, iron, bromine, iodine, calcium, and nitrate, for example, are known, and passivation layers may comprise various materials (e.g., metal oxides, metal nitrides, metal oxynitrides). Regarding the chemical reactions at the analyte solution/passivation layer interface, the surface of a given material employed for the passivation layer of the ISFET may include chemical groups that may donate protons to or accept protons from the analyte solution, leaving at any given time negatively charged, positively charged, and neutral sites on the surface of the passivation layer at the interface with the analyte solution.

With respect to ion sensitivity, an electric potential difference, commonly referred to as a "surface potential," arises at the solid/liquid interface of the passivation layer and the analyte solution as a function of the ion concentration in the sensitive area due to a chemical reaction (e.g., usually involving the dissociation of oxide surface groups by the ions in the analyte solution in proximity to the sensitive area). This surface potential in turn affects the threshold voltage of the ISFET; thus, it is the threshold voltage of the ISFET that varies with changes in ion concentration in the analyte solution in proximity to the sensitive area. As described in Rothberg, since the threshold voltage VTH of the ISFET is sensitive to ion concentration, the source voltage VS provides a signal that is directly related to the ion concentration in the analyte solution in proximity to the sensitive area of the ISFET.

Arrays of chemically-sensitive FETs ("chemFETs"), or more specifically ISFETs, may be used for monitoring reactions—including, for example, nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Such use of ChemFET (or ISFET) arrays involves detection of analytes in solution and/or detection of change in charge bound to the chemFET surface (e.g. ISFET passivation layer).

Research concerning ISFET array fabrication is reported in the publications "A large transistor-based sensor array chip for direct extracellular imaging," M. J. Milgrew, M. O. Riehle, and D. R. S. Cumming, Sensors and Actuators, B: Chemical, 111-112, (2005), pp. 347-353, and "The development of scalable sensor arrays using standard CMOS technology," M. J. Milgrew, P. A. Hammond, and D. R. S. Cumming, Sensors and Actuators, B: Chemical, 103, (2004), pp. 37-42, which publications are incorporated herein by reference and collectively referred to hereafter as "Milgrew et al." Descriptions of fabricating and using ChemFET or ISFET arrays for chemical detection, including detection of ions in connection with DNA sequencing, are contained in Rothberg. More specifically, Rothberg describes using a chemFET array (in particular ISFETs) for sequencing a nucleic acid involving incorporating known nucleotides into a plurality of identical nucleic acids in a reaction chamber in contact with or capacitively coupled to chemFET, wherein the nucleic acids are bound to a single bead in the reaction chamber, and detecting a signal at the chemFET, wherein detection of the signal indicates release of one or more hydrogen ions resulting from incorporation of the known nucleotide triphosphate into the synthesized nucleic acid.

FIG. 1 is a cross-sectional diagram depicting an embodiment of a physical structure of an ion-sensing system 20 that can include an ISFET 24, a solution 28 provided at an ion-sensitive surface 32 of the ISFET 24, and an electrode 36 in the solution 28 providing a reference voltage VREFA. The ISFET 24 can be fabricated in a CMOS process, and include n-type source and drain diffusion regions 40, 44 formed in a p-type silicon substrate 48, source and drain connections 52, 56, a gate oxide layer 60 over a channel-forming region 64 between the source and drain 40, 44, a floating gate structure 68 formed over the gate oxide 60, and a passivation layer 72 formed over the gate structure 68. The floating gate structure 68 can include a polysilicon gate 78 and one or more metal layers 76 and via interconnections 80. The source and drain connections 52, 54 can also include one or more metal layers 76 and via interconnections 80. A dielectric isolation 84 can separate these various structures.

In operation, the reference voltage VREFA can be supplied to the electrode 36 in the solution 28, and the source and drains 40, 44 of the ISFET 24 can be electrically connected to readout circuitry (not shown) through the source and drain connection structures 52, 56. The gate 78 of the ISFET 24 may have no direct electrical connection to other circuits, and thus can be an electrically floating structure. The effect of the ion concentration on the operation of the ISFET 24 can be modeled as a dependence of a threshold voltage of the ISFET 24 on the ion concentration in the solution 28 resulting from an electrochemical interaction between the ion-sensitive passivation surface 32 of the ISFET 24 and ions in the adjacent solution 28. The ion-sensing system 20 can thus determine the ion concentration from a threshold voltage change, itself determined by measuring a current or voltage change at the source or drain 40, 44 of the ISFET 24, given a known reference voltage VREFA and readout circuit type and operation.

However, problems exist with the ion-sensing system 20 of FIG. 1 and its use to detect the ion concentration of the solution 28. The change to the voltage or current at the source or drain 40, 44 of the ISFET 24, and thus in the readout circuit, induced by the change in threshold voltage can be small and difficult to accurately measure. Additionally, the threshold voltage itself can be a non-linear function of other variables, such as the voltage across the source 40 to the substrate 48 (i.e., body) of the ISFET 24. This can limit the linearity of the threshold voltage calculations, if the source-to-body voltage is allowed to vary, or limit the type of readout circuit that can be used, if the source-to-body voltage is to be maintained relatively constant to preserve linearity. In a similar vein, both dynamic range and signal-to-noise performance of the ion-sensing system 20 of FIG. 1 are concerns. Overall, these concerns can necessitate the use of complex, and thus space-consuming and costly, readout circuits, or limit the performance metrics that can be achieved using this ion-sensing system 20.

Thus, a need exists for a way to achieve improved speed, accuracy, linearity and other performance metrics when measuring ion concentration in a solution, but while still utilizing devices that can be manufactured in bulk using a CMOS process.

BRIEF DESCRIPTION OF THE DRAWINGS

So that features of the present invention can be understood, a number of drawings are described below. However, the appended drawings illustrate only particular embodiments of the invention and are therefore not to be considered limiting of its scope, for the invention may encompass other equally effective embodiments.

FIGS. 11A-11D are cross-sectional, potential and charge diagrams depicting embodiments of operation of the pixel circuit depicted in FIG. 10.

DETAILED DESCRIPTION

An ion-sensitive circuit can include a charge accumulation device, to accumulate a plurality of charge packets as a function of an ion concentration of a fluid, and at least one control and readout transistor, to generate an output signal as a function of the accumulated plurality of charge packets, the output signal representing the ion concentration of the solution. The charge accumulation device can include a first charge control electrode above a first electrode semiconductor region, an electrically floating gate structure above a gate semiconductor region and below an ion-sensitive passivation surface, a second charge control electrode above a second electrode semiconductor region, and a drain diffusion region. The first control electrode can control entry of charge into a gate semiconductor region in response to a first control signal. The ion-sensitive passivation surface can be configured to receive the fluid. The second charge control electrode can control transmission of the plurality of charge packets out of the gate semiconductor region and into the drain diffusion region in response to a second control signal. The drain diffusion region can receive the plurality of charge packets from the gate semiconductor region via the second electrode semiconductor region.

The ion-sensitive circuit can operate according to a method to detect the ion concentration of the fluid. The method can include (i) passing the fluid having the ion concentration over the ion-sensitive passivation surface of the charge accumulation device; (ii) individually forming, one at a time, the plurality of charge packets in the gate semiconductor region of the charge accumulation device as a function of the ion concentration in the fluid; (iii) applying a control signal to the second control electrode of the charge accumulation device to control transmission of the charge packets one at a time from the gate semiconductor region; (iv) accumulating the plurality of charge packets at the drain diffusion region of the charge accumulation device at a selectable charge packet accumulation frequency; and (v) generating an output signal using the at least one control and readout transistor as a function of the accumulated plurality of charge packets at the drain region at a selectable output signal generation frequency, wherein the output signal represents a measure of the ion concentration in the fluid.

Figure 2:
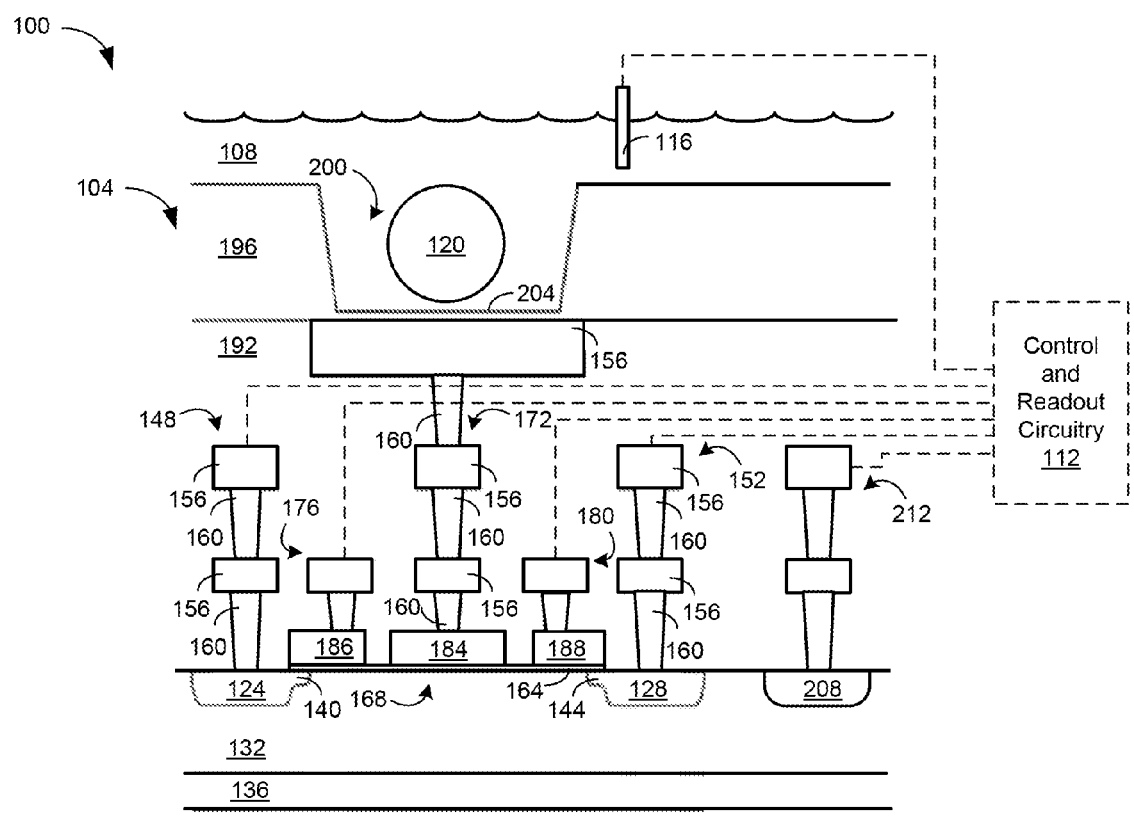
FIG. 2 is a partially cross-sectional, partially schematic diagram of an ion-sensing system including a ion-sensitive charge accumulation device.

FIG. 2 depicts a partially cross-sectional, partially schematic view of an embodiment of an ion-sensing system 100, having an ion-sensitive charge-accumulation device 104, that can detect ion concentration in a solution 108 to perform DNA sequencing and other applications. The ion sensing system 100 can include the charge-accumulation device 104, a control and readout circuit 112, an electrode 116, the solution 108 and a micro-particle or micro-bead 120. In FIG. 2, the charge-accumulation device 104, electrode 116, solution 108 and micro-particle 120 are depicted in a cross-sectional representation, while the control circuit 112, and its connection to terminals of the charge-accumulation device 104 are depicted schematically. For convenience, the schematic portions of FIG. 2 are indicated by dashed lines.

The charge accumulation device 104 can be fabricated in a CMOS process and be part of an integrated circuit including the charge-accumulation device 104 and the control and readout circuit 112. N-type source and drain diffusion regions 124, 128 can be formed in a p-type epitaxial layer 132 formed on a p-type silicon substrate 136. The source and drain diffusion regions 124, 128 can have lightly-doped portions 140, 144 with relatively less doping than other portions of the drain and diffusion regions 124, 128. Source and drain connections 148, 152 can include one or more metal layers 156 and via interconnections 160. A gate oxide layer 164 can be formed over a region 168 of the p-type epitaxial layer 132 between the source and drain 124, 128, and a floating gate structure 172 and first and second control electrode structures 176, 180 can formed over the gate oxide 164. The gate oxide 164 can include a material such as silicon dioxide. The floating gate structure 172 can include a n-type polysilicon gate 184 and one or more metal layers 156 and via interconnections 160. The control electrode structures 176, 180 can also include first and second n-type polysilicon electrodes 186, 188, respectively, and one or more metal layers 156 and via interconnections 160. The metal layers 156 and vias 160 can each include one or more layers of conductive materials such as tungsten, aluminum, copper, titanium, and nitrides and silicides thereof. Dielectric isolation 192 between these various structures can include one or more layer of silicon oxide, borophosphosilicate glass, or combinations thereof. A passivation layer 196 can be formed over the gate structure 172 and dielectric isolation 196, and include a well 200 having an ion-sensitive surface 204 to accommodate the micro-particle 120 (or micro-bead 120), which can have a plurality of replicated DNA strands attached to its surface. The passivation layer 196 can include a material such as silicon nitride, silicon on/nitride, and polyimide. A substrate connection diffusion region 208 and can have an associated connection structure 212 similar to the drain and source connection structures 148, 152.

Reference to diffusion regions 124, 128 as source and drain diffusion regions 124, 128 is for convenience of reference herein. These diffusion regions 124, 128, however, do not need to have all the same properties as a source and drain of a transistor. Instead, the source and drain diffusion regions 124, 128 can also be referred to as simply diffusion regions 124, 128, without necessarily implying transistor source and drain functionality. In some instances, however, as is apparent from the description herein, the diffusion regions 124, 128 may indeed have properties like those of a source and drain of a transistor.

The ion-sensing system 100 can be used to perform DNA sequencing or other applications involving the sensing of ions in the solution 108. A plurality of the DNA-strand-bearing micro-particles 120 can be introduced to a surface of an integrated circuit containing a plurality of the charge-accumulation devices 104 depicted in FIG. 2, with the micro-particles 120 settling into the wells 200 of the passivation layer 196. A plurality of different solutions 108 can be sequentially introduced to and received by the surface of the integrated circuit, including in the wells 200 in the passivation layer 196. Each of the solutions 108 in the sequential series of solutions can include a different nucleotide or nucleobase. Each solution, or reagent, may or may not react with the DNA strands attached to the micro-particle 120, depending on whether the solution's particular nucleotide or nucleobase matches or compliments a currently reactive position along the sequence of nucleobases of the attached DNA strands. When a particular solution 108 in the sequence of administered solutions does react with the DNA strands, a plurality of ions, such as, e.g., protons (e.g., hydrogen H+ ions), pyrophosphate (i.e., PPi), or both, may be released. The ion-sensitive charge-accumulation device 104 can detect the concentration of ions in the solution 108, according to principles of its operation discussed herein, to provide data as to the identity of the nucleobase of the currently reactive position of the attached DNA strands, thereby providing data to sequence the strands.

In operation, the ion-sensitive charge-accumulation device 104 can generate and accumulate a plurality of charge packets 216 (shown, e.g., in FIGS. 3A-3D) as a function of and in response to ion concentrations in the solution 108 provided to the ion-sensitive surface 204 of the well 200 in the passivation layer 196, using potential energy barriers and gradients created through the application of control signals to the source 124, drain 128, first and second control electrodes 186, 188 by the control and readout circuitry 112. FIGS. 3A-D depict embodiments of a plurality of cycles of operation of the charge-accumulation device 104 to generate and accumulate charge packets in response to ion concentrations in the solution 108. Each of FIGS. 3A-3D can depict a complete cycle of an embodiment of operation of the charge accumulation device 104. The top of each of FIGS. 3A-3D depicts a simplified partially cross-sectional, partially schematic representation of the charge-accumulation device 104, showing only the source and drain regions 124, 128, the gate oxide 164, the floating gate 184, and the first and second control electrodes 186, 188. For convenience of illustration and explanation, other components of the charge-accumulation device 104 are omitted from the depictions, although omitted components can be present in actual embodiments. In each figure, below the representation of the charge-accumulation device 14 are four diagrams depicting potential energies and charge present in the charge accumulation device 104 at different stages during the operational cycle of the device 104. Each of these diagrams is aligned to and depicts the potential energy and charge in specific spatial regions of the charge accumulation device 104 depicted at the top of the figure, so that each diagram therefore depicts the potential energy and charge in the n-type source and drain regions 124, 128 and in the p-type epitaxial regions under the control electrodes 186, 188 and the floating gate 184.

Figures 3A, 3B, 3C, 3D:
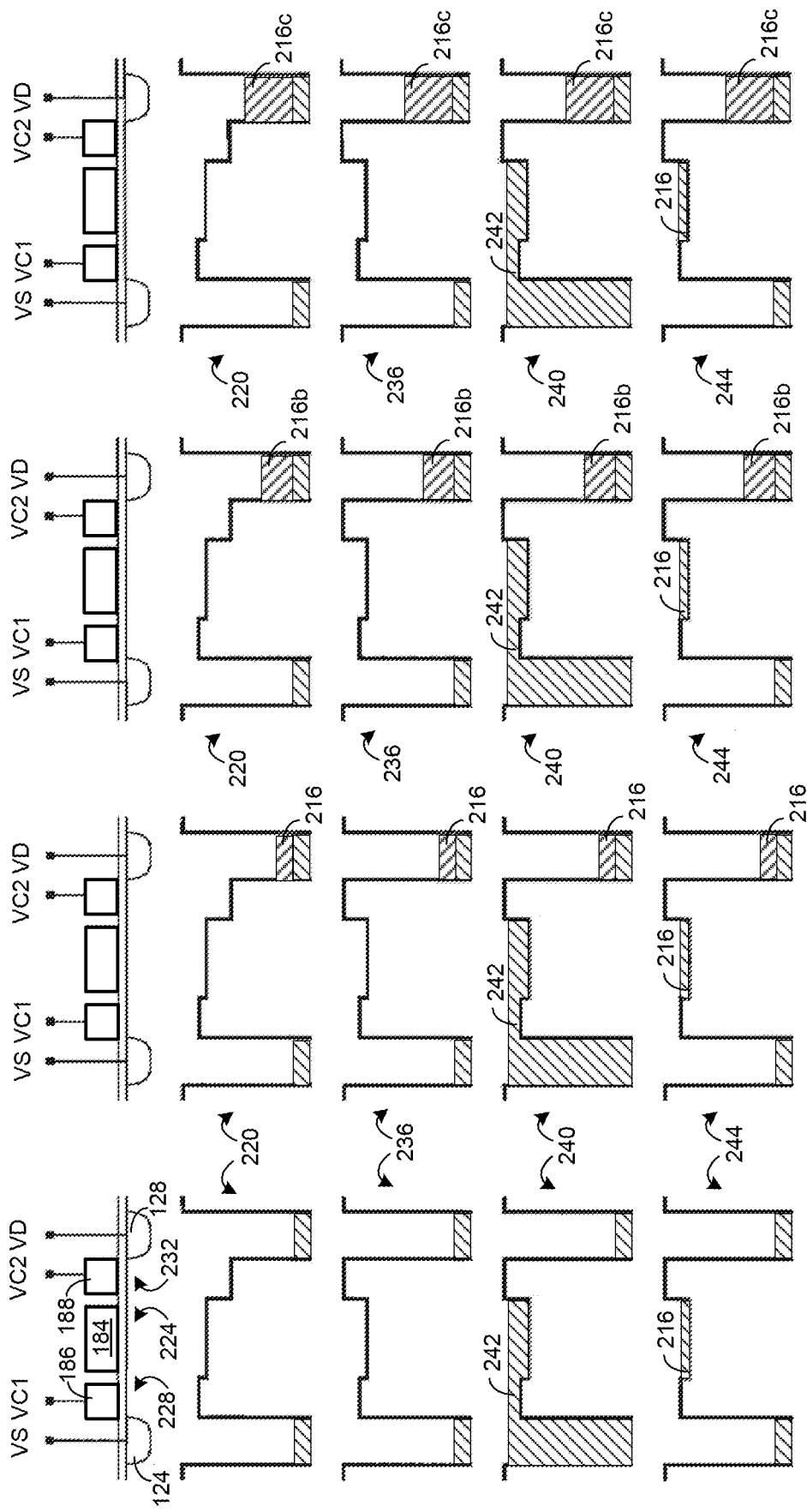
FIGS. 3A-3D are cross-sectional, potential and charge diagrams depicting an embodiment of an operational cycle of the ion-sensitive charge accumulation device.
Figure 4:
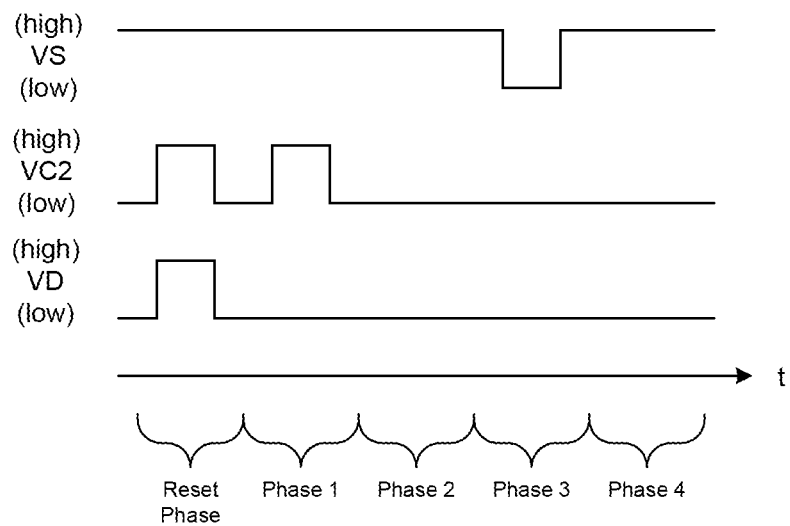
FIG. 4 is a signal diagram depicting an embodiment of control signals for controlling the operation of the charge accumulation device.

FIG. 4 is a signal diagram depicting an embodiment of a plurality of control signals that can be used to control the operation of the charge accumulation device 104 depicted in FIGS. 3A-3D. In FIG. 4, control signals VS, VD, VC2 delivered to the source 124, drain 128 and second control electrode 188 can vary between voltage values representing logic low and logic high states, such as lower and upper power supply voltages. Another control signal VC1 (not shown) can be delivered to the first control electrode 186, and may not represent a logic state and instead may assume an intermediate voltage value, such as a value between lower and upper power supply voltages. Other embodiments of control signals are possible, such as various combinations of control signals that vary between voltage values representing logic low and logic high states (such as lower and upper power supply voltages) and control signals that do not represent logic states and instead assume intermediate voltage values (such as a value between lower and upper power supply voltages). Embodiments of control signals can also be a function of specific embodiments of the physical structure of the charge-accumulation device 104. For example, the height of the gate oxide 164 between the first control electrode 186, floating gate 184, and second control electrode 188 can be selected to control the relative impact on potential energy in the charge accumulation device 104 of a given control voltage delivered to the first control electrode 186, floating gate 184 and second control electrode 188, respectively.

Prior to a first phase of the operational cycle depicted in FIG. 3A, in a pre-cycle reset phase (not shown in FIG. 3A), any charge remaining in the charge accumulation device 104 from a previous operation of the device 104 can be removed by delivering suitable control signals to the source 124, drain 128 and control electrodes 186, 188. In the embodiment depicted in FIG. 4, a high voltage can be delivered to the drain 124 and second control electrode 188, a low voltage to the source 124, and an intermediate voltage to the first control electrode 186 to clear any charge from a previous operation of the device 104.

In a first phase 220 of the operational cycle depicted in FIG. 3A, any charge packet 216 formed in the semiconductor region 224, e.g., p-type epitaxial region 224, under the floating gate 184 can be transferred to the drain diffusion region 208. This can be done by creating a potential gradient in the semiconductor regions 228, 224, 232 under the first control electrode 186, gate 184, and second control electrode 188 to direct the charge under the gate 184 to move to the drain diffusion region 208. Specifically, a relatively lower potential, and thus a relatively higher barrier to electron flow, can be created in the region 228 under the first control electrode 186, and a relatively higher potential, and thus a relatively lower barrier to electron flow, can be created in the region 232 under the second control electrode 188.

The potential diagrams of FIGS. 3A-3D, and other potential diagrams depicted and discussed herein, follow the convention that increasing potential energies correspond to downward directions in the potential energy diagrams. Thus, relatively higher potential energies are depicted by spatially lower indications in the diagrams. Relatively higher potential energies can be induced in p-type regions by applying relatively higher voltages to the control electrodes 186, 188 or such manifesting on the floating gate 184, and can represent a lower potential barrier to the accumulation or passage of electrons in p-type regions. By contrast, relatively lower potential energies can be induced in p-type regions by relatively lower voltages applied to the control electrodes 186, 188 or such manifesting on the floating gate 184, and can represent a higher potential barrier to the accumulation or passage of electrons in p-type regions.

Returning to FIG. 3A, the first stage potential energy gradient can be created in the regions 228, 224, 232 under the first control electrode 186, floating gate 184 and second control electrode 188 by application or manifestation of increasing voltages to the first control electrode 186, floating gate 184 and second control electrode 188, respectively, assuming a uniform gate oxide thickness. Alternatively, this potential energy gradient can also be created with other applied or manifested voltages and a non-uniform gate oxide thickness. FIG. 4 depicts an embodiment in which a high voltage can be delivered to the second control electrode 188 and source 124, a low voltage can be delivered to the drain 124, and the intermediate voltage to the first control electrode 186 in the first phase. Other embodiments of first phase control signals are possible.

Note that, because FIG. 3A depicts the first of several cycles of operation of the charge accumulation device 104 after a pre-cycle reset phase has removed any remaining charge packets 216 from a previous operation, no charge packet 216 has yet developed under the gate 184, and thus no charge packet 216 is transferred to the drain 128 in the first phase 220 depicted in FIG. 3A. However, the transfer during the first phase 220 of the charge packet 216 from under the gate 184 to the drain region 128 can be illustrated by the succeeding cycles depicted in FIGS. 3B-3D.

In a second phase 236 of the operational cycle depicted in FIG. 3A, the potential barrier under the second control electrode 188 can be raised to prevent charge packet flow from the region 224 under the gate 184 through the region 232 under the second electrode 188 to the drain region 128. FIG. 4 depicts an embodiment of second phase control signals in which a low voltage can be delivered to the second control electrode 188 and drain 128, a high voltage to the source 124, and the intermediate voltage to the first control electrode 186. Other second phase control signal embodiments are possible.

In a third phase 240 of the operational cycle depicted in FIG. 3A, charge, e.g., electrons, can be injected into the p-type region 224 under the floating gate 184 from the n-type source region 124. Because the potential barrier under the second electrode 188 has been raised during the second phase 236 to be higher than under the first control electrode 186 and floating gate 184, the charge 242 can flood the charge accumulation device 104 from the source 124 to under the first control electrode 186 and the floating gate 184, but not under the second control electrode 188. Charge 242 can be injected into the charge accumulation device 104 through the source 124 in various ways, such as through the use of a current source or charge pump selectively injecting charge into the source 124, or by applying a suitable voltage to the source 124 in the context of voltages supplied to or manifesting elsewhere in the charge accumulation device 104, e.g., on the first control electrode 186 and floating gate 184. FIG. 4 depicts an embodiment of the control signals in which a low voltage can be delivered to the source 124, while relatively higher voltages can be delivered or manifest on the first control electrode 186 and floating gate 184 (e.g., the intermediate voltage delivered to the first control electrode 186 and the potential induced on the floating gate 184 by the ion concentration in the solution 108).

In a fourth phase 244, the charge injection from the source 124 into the charge accumulation device 104 can be ended, and excess charge in the source 124 and under the first control electrode 186 withdrawn. However, because a potential differential can exist between under the first control electrode 186 and under the floating gate 184, a packet of charge 216 can remain under the floating gate 184 as a result of this potential difference. This potential difference can be a function of the voltage VC1 applied to the first control electrode 186 and the voltage manifesting on the floating gate 184 due to the ion concentration in the solution 104. Thus, the size of the charge packet 216 remaining under the floating gate 184 in the fourth phase 244 can be a function of the voltage VC1 applied to the first control electrode 186 and the voltage manifesting on the floating gate 184 due to the ion concentration in the solution 108, and thus a measure of the ion concentration in the solution 108, given a known voltage VC1 applied to the first control electrode 186.

Finally, in a first phase 220 of the next cycle of operation of the charge accumulation device 104, depicted in FIG. 3B, and as discussed above in regard to the first phase 220 of the first cycle of operation depicted in FIG. 3A, the charge packet 216 remaining under the floating gate 184 after the fourth stage 244 of the first cycle of operation can be transferred from under the gate 184, through the region 232 under the second control electrode 188, and into the drain diffusion region 128, where it can be maintained. Thus, after a single cycle of operation, a single charge packet 216, having a size that can be a measure of the ion concentration of the solution 108, can have been collected at the drain 128 of the charge accumulation device 104.

Although the charge accumulation device 104 can provide a measure of the ion concentration in the solution 104 with just a single charge packet 216 collected at the drain 128, the charge accumulation device 104 can also detect and provide a measure of the ion concentration in the solution 108 by collecting a plurality of charge packets 216 at the drain 128 over a plurality of cycles of operation of the charge accumulation device 104. The collected plurality of charge packets 216 can also provide a measure of the ion concentration in the solution 108. FIGS. 3B-3D depict second, third and fourth cycles of operation of the charge accumulation device 104 following the first cycle of operation depicted in FIG. 3A. After each cycle, another charge packet 216 can be accumulated at the drain 128 as a function of the ion concentration. In FIG. 3B, in a first phase 220 of the second cycle, a first charge packet 216 can be trapped at the drain 128 after the first cycle depicted in FIG. 3A. In FIG. 3C, in a first phase 220 of the third cycle, first and second charge packets 216b can be accumulated at the drain 128 following the second cycle depicted in FIG. 3B. In FIG. 3D, in a first phase 220 of the fourth cycle, first, second and third charge packets 216c can be accumulated at the drain 128 following the third cycle depicted in FIG. 3C.

Figure 1:
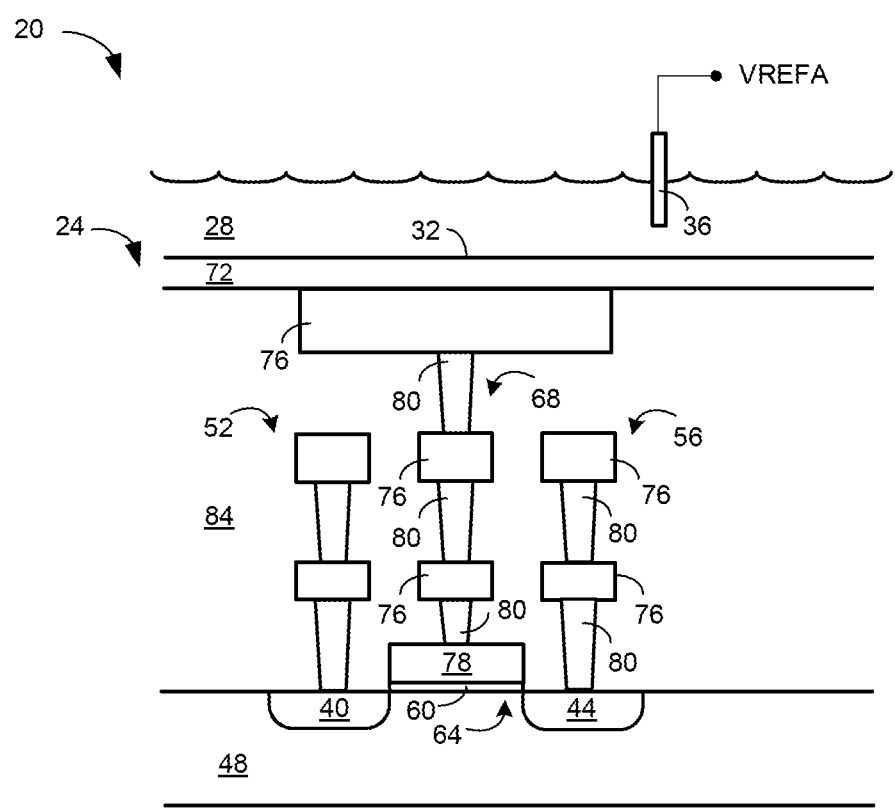
FIG. 1 is a cross-sectional diagram depicting an embodiment of an ion-sensing system including an ion-sensitive field effect transistor.

Providing a measure of the ion concentration in the form of an accumulated plurality of charge packets 216 can provide a measure having an increased signal level and signal-to-noise ratio, improved performance matching of a plurality of charge accumulation devices 104, and reduced flicker noise, in comparison to both providing a measure of the ion concentration in the form of only a single charge packet 216 and in the form of a threshold voltage variation, as discussed above in regard to FIG. 1. For example, due to the thermal activity of charges such as holes and electrons, generated charge packets are typically associated with a degree of noise. In one embodiment, the accumulation of a single charge packet may be accompanied by a noise charge error proportional to $k \cdot T \cdot C$, where k is Boltzmann's constant, T is the temperature in Kelvins, and C is the capacitance of the charge gathering region under the floating gate. When the charges are electrons, the voltage noise error for each collected packet can be equal to $(\sqrt{k \cdot T \cdot C})/q$, where q is the charge of an electron, and C is equal to the oxide capacitance Cox multiplied by the area of the floating gate 184. However, the signal-to-noise ratio SNR of an output signal based on the accumulation of a plurality of charge packets can be proportional to the square root of $(2 \cdot n \cdot C/k \cdot T)$, where n is the number of packets 216 accumulated, i.e., the number of operational cycles of the charge accumulation device 104 utilized to provide a single ion concentration measurement. Thus, the signal-to-noise ratio of the ion concentration measurement can increase in proportion to the square root of the number of packets 216 in a single measurement.

After accumulation at the drain 128 of the charge accumulation device 104, the plurality of charge packets 216 can be converted to an output signal or transferred out of the charge accumulation device using embodiments of the control and readout circuitry 112. The control and readout circuit 112 can control various aspects of both the cyclical operation of the charge accumulation device 104 and generation of an output signal based on the accumulated charge packets 216. The control and readout circuit 112 can control the charge accumulation device 104 by providing control signals to the source 124, drain 128, first control electrode 186 and second control electrode 188 to accumulate packets 216 at a selectable predetermined accumulation frequency. The accumulation frequency can be the frequency of operation of a single operational cycle of the charge accumulation device 104. The accumulation frequency can be selected based on or as a function of the anticipated rate of change of the ion concentration in the solution, the performance characteristics of the charge accumulation device 104 and control and readout circuitry 112, or a combination thereof. The control and readout circuit 112 can also control the generation of an output signal based on the charge packets 216 accumulated by the charge accumulation device 104 by providing control signals thereto to generate an output signal or transfer accumulated pluralities of charge packets 216 out of the charge accumulation device 104 at a selectable output generation frequency. The output generation frequency can be the frequency of generation of a single output signal value from the accumulated packets 216 in the charge accumulation device 104. The output generation frequency can be selected to be based on or be a function of the anticipated rate of change of the ion concentration in the solution 108, the performance characteristics of the charge accumulation device 104 and the control and readout circuitry 112, or a combination thereof. When the output signal is based on a plurality of accumulated charge packets 216, the output generation frequency can be less than the charge packet accumulation frequency.

Figure 5:
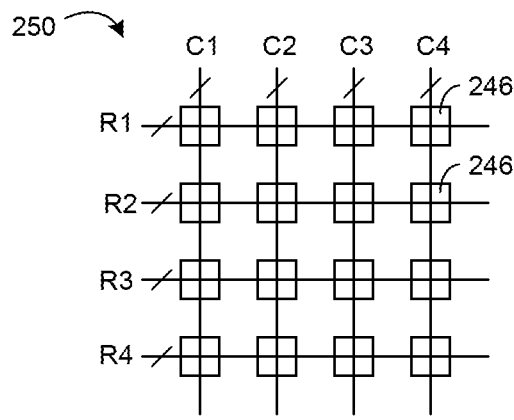
FIG. 5 is a schematic diagram depicting an embodiment of an ion-sensitive pixel array having a plurality of pixel circuits, each including the charge accumulation device and control and readout transistors.

A single charge accumulation device 104, along with associated portion of the control and readout circuitry 112 dedicated to that device 104, can represent a single ion-sensing pixel 246 in an array 250 of a plurality of ion-sensing pixels 246. FIG. 5 depicts an embodiment of an ion-sensing pixel array 250 having a plurality of ion-sensing pixels 246. Each pixel circuit 246 can include a charge accumulation device 104 and an associated portion of the control and readout circuit 112. The associated portion of the control and readout circuit 112 can be part of and dedicated to the particular pixel 246. The pixel array can be arranged into a plurality of rows and columns of pixels 246. The pixel array 250 can be controlled, addressed and have data input and output by a plurality of row and column control, addressing and data lines, including one or more row control, addressing and data lines R1-Rx, collectively referred to as row lines R1-Rx, and one or more column control, addressing and data lines C1-Cx, collectively referred to as column lines C1-Cx, for each row and each column.

Figure 6:
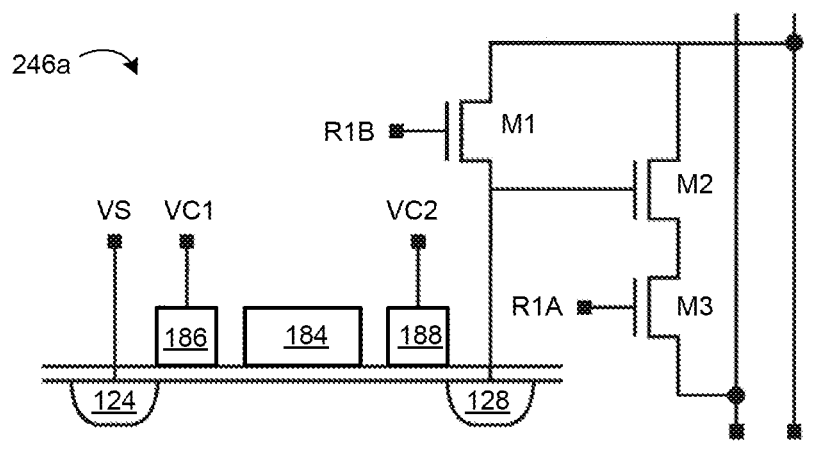
FIG. 6 is a partially cross-sectional, partially schematic diagram depicting an embodiment of a pixel circuit including the charge accumulation device and control and readout transistors.

FIG. 6 depicts an embodiment of an ion-sensing pixel 246a having embodiments of the charge accumulation device 104 and associated control and readout circuit portion 112. Note that FIG. 6 again depicts a simplified representation of the charge accumulation device 104, however embodiments of the depicted pixel 246a can include other components of the charge accumulation device 104, such as the additional components depicted in FIG. 2. The embodiment of FIG. 6 can be referred to as a three transistor, three electrode, or 3T3E, pixel 246. The control and readout circuit 112 can include three transistors, including a reset transistor M1 and a pair of readout transistors M2, M3. The charge accumulation device 104 can have three electrodes, including the first and second control electrodes 186, 188 and the floating gate 184. The control and readout circuit 112 can receive a plurality of column lines, including first and second column lines C1A, C1B, and a plurality of row lines, including first and second row lines R1A, R1B.

For purposes of discussion with reference to sources and drains, etc., it will be assumed that the control and readout transistors M1, M2, M3 in the pixel embodiment 246a of FIG. 6, and in other pixel embodiment depictions discussed herein, are NMOS transistors. However, in other pixel embodiments, the control and readout transistors can be either NMOS or PMOS transistors, or any combination thereof. In FIG. 6, the first readout transistor M2 can have a gate connected to the drain region 128 of the charge accumulation device 104, a source connected to a drain of the second readout transistor M3, and a drain connected to the second column line C1B. The second readout transistor M3 can have a gate connected to the first row line R1A, a source connected to the first column line C1A, and a drain connected to the source of the first readout transistor M2. The reset transistor M1 can have a source connected to the drain 128 of the charge accumulation device 104, a gate connected to the second row line R1B, and a drain connected to the second column line C1B.

The embodiment of the control and readout circuit 112 of FIG. 6 can be used to control the charge accumulation device 104 and generate an output signal in conjunction with the operation of the charge accumulation device 104 depicted in FIGS. 3A-3D and FIG. 4. In a reset operation, the reset transistor M1 and the second row and column lines R1B, C1B can be used to reset the charge accumulation device 104 in the pre-cycle reset phase, as discussed above. For example, a logic high signal, or high-valued voltage such as an upper power supply, can be delivered to the second row and column lines R1B, C1B while a logic low signal, or low-valued voltage such as a low power supply, can be delivered to the first row line R1A, to turn on the rest transistor M1 while turning off the second readout transistor M3. This can deliver a high voltage value to the drain region 128 of the charge accumulation device 104, resulting in the clearing out of any charge packets 216 accumulated at the drain 128, thus resetting the charge accumulation device 104.

In a readout operation, the readout transistors M2, M3 and the first row and column lines R1A, C1A can be used to generate an output signal as a function of the charge packets 216 accumulated at the drain region 128 of the charge accumulation device 104 after one or more cycles of operation of the device 104, as discussed above. For example, a logic high signal or high-valued voltage such as an upper power supply, or alternatively an intermediate-valued voltage such as a voltage between the upper and lower power supplies, can be delivered to the first row line R1A while a logic low signal, or low-valued voltage such as a low power supply, can be delivered to the second row line R1B, essentially activating the first and second readout transistors M2, M3 while turning off the reset transistor M1. In this mode, the first and second readout transistors M2, M3 can act as an amplifier to convert the one or more charge packets 216 accumulated at the drain region 128 of the charge accumulation device 104 to a voltage output signal on the first column line C1A. The first readout transistor M2 can be modeled as operating in a source follower configuration, receiving an input voltage from the drain 128 of the charge accumulation device 104 and providing an intermediate output voltage at its source to the drain of the second readout transistor M3. The conversion of the charge packets 216 to an input voltage at the drain 128 of the charge accumulation device 104 can be an inherent result of the accumulation of charge at the drain 128. The second readout transistor M3 can be modeled as operating in a cascode configuration with respect to the source follower first readout transistor configuration, thereby boosting the gain of the two transistor combination in comparison to the source follower alone. The second readout transistor M3 can receive the intermediate output from the source of the source follower and provide the output voltage to the first column line C1A at this source.

Figure 7:
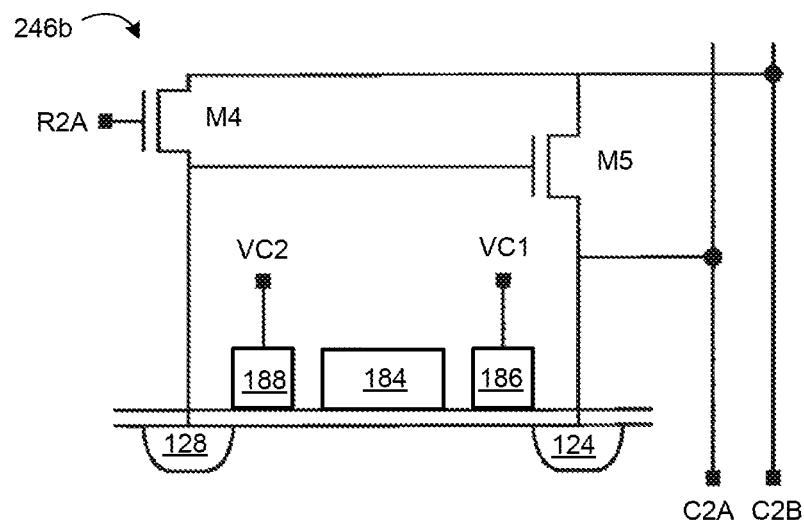
FIG. 7 is a partially cross-sectional, partially schematic diagram depicting another embodiment of a pixel circuit including the charge accumulation device and control and readout transistors.

FIG. 7 depicts another embodiment of an ion-sensing pixel 246b having embodiments of the charge accumulation device 104 and associated control and readout circuit portion 112. Note that FIG. 7 again depicts a simplified representation of the charge accumulation device 104, however embodiments of the depicted pixel 246b can include other components of the charge accumulation device 104, such as the additional components depicted in FIG. 2. The embodiment of FIG. 7 can be referred to as a two transistor, three electrode, or 2T3E, pixel. The control and readout circuit 112 can include two transistors, including a reset transistor M4 and a readout transistor M5, and the charge accumulation device 104 can have three electrodes, including the first and second control electrodes 186, 188 and the floating gate 184. The control and readout circuit 112 can receive a row line R2A and a plurality of column lines, including first and second column lines C2A, C2B.

The pixel embodiment 246b of FIG. 7 can reduce the number of readout transistors, in comparison to the pixel embodiment 246a of FIG. 6, by management of the voltage at the drain 128 of the charge accumulation device 104 to eliminate the need for a row select functionality served by the first row line R1A of the pixel embodiment 246a of FIG. 6. The drain 128 in each of FIGS. 7 and 9, also called a floating diffusion 128, can have the property of a capacitance. The row select device can be eliminated by managing the floating diffusion potential when the pixel 246b is not active. The gate tied to the floating diffusion 128, for example M5 in FIG. 7, can remain at a low potential in order to disable the source follower M5 when not in use. Therefore, after the pixel 246b has been read out, the floating diffusion 128 can be sampled to a low potential and then left at that potential until the pixel 246b is read again. A reason the potential stays low can be that the floating diffusion 128 acts like a capacitor that holds the low voltage sampled onto it.

In FIG. 7, note that the depicted spatial arrangement of the first and second control electrodes 186, 188 is reversed from that shown in previous figures, with the first control electrode 186 depicted on the right-hand side and the second control electrode 188 depicted on the left-hand side. Again, for purposes of discussion with reference to sources and drains, etc., it will be assumed that the control and readout transistors are NMOS transistors, however the control and readout transistors in any of the pixel embodiments can be either NMOS or PMOS transistors, or any combination thereof. The reset transistor M4 can have a source connected to the drain 128 of the charge accumulation device 104, a gate connected to the row line R2A, and a drain connected to the second column line C2B. The readout transistor M5 can have a gate connected to the drain region 128 of the charge accumulation device 104 (and thus also the source of the reset transistor M4), a source connected to the source 124 of the charge accumulation device 104 and the first column line C2A, and a drain connected to the second column line C2B.

FIGS. 8A-8D depict an embodiment of the operation of the pixel embodiment 246b of FIG. 7 to accumulate a plurality of charge packets 216 as a function of the solution ion concentration and generate an output signal as a function of the accumulated charge packets 216. FIGS. 8A-8D depict a plurality of complete cycles of an embodiment of operation of the charge accumulation device 104. Similarly to FIGS. 3A-3D, the top of each of FIGS. 8A-8D depicts a simplified partially cross-sectional, partially schematic representation of the pixel 246, including the charge-accumulation device 104 and control and readout transistors M4, M5. For convenience of illustration and explanation, other components of the charge-accumulation device 104 and control and readout transistors M4, M5 are omitted from the depictions, although omitted components can be present in actual embodiments. In each figure, below the representation of the charge-accumulation device 104 and control and readout transistors M4, M5 are four diagrams depicting, in a manner spatially aligned to the pixel representation above, potential energies and charge accumulation in the charge accumulation device 104 and control and readout transistors M4, M5 at different phases of an operational cycle of the pixel 246b.

In a reset phase 254, the reset transistor M4 and the row and second column line R2A, C2B can be used to reset the charge accumulation device 104. A logic high signal, or high-valued voltage such as an upper power supply, can be delivered to the row and second column lines R2A to turn on both the rest transistor M4 and the readout transistor M5. This can deliver a high voltage value to both the drain 128 and source 124 of the charge accumulation device 104, resulting in the clearing of any charge accumulated at the drain and source 128, 124 of the charge accumulation device 104, and thus resetting the device 104.

In a first phase 258 of the operational cycle, the reset transistor M4 can be turned off and a potential barrier raised (i.e., a low potential created) under the second electrode 188, preparing the charge accumulation device 104 for generating a charge packet 216 under the floating gate 184. The reset transistor M4 can be turned off and the low potential under the second electrode 188 created by delivering a logic low or low-valued voltage to the row line R2A and second control electrode 188. Note that at the end of the first phase 258, a high potential, and thus a low potential barrier, is left existing under the gate of the readout transistor M4.

In a second stage 262 of the operational cycle, charge, e.g., electrons, can be injected into the p-type region 224 under the floating gate 184 from the n-type source region 124 of the charge-accumulation device 104. The charge 264 can flood the charge accumulation device 104 from the source 124 to under the floating gate 184, but not under the second control electrode 188. Charge can be injected into the charge accumulation device 104 through the source 124 in various ways, such as through the use of a current source or charge pump selectively injecting charge into the source 124, or by applying a suitable voltage to the source 124 in the context of voltages supplied to or manifesting on the first control electrode 186 and floating gate 184, such as, e.g., a logic-low or low-valued voltage. The charge can be injected under the floating gate 184 through the source 124 using the first column line C2A, and thus charge 265 can simultaneously be injected into the readout transistor M4, including both its source and drain regions and under its gate, due to the low potential barrier left existing under the gate of this transistor M4 after the first phase 258 of the operational cycle.

In a third stage 266, the charge injection into the charge accumulation device and readout transistor can be ended, and excess charge in these devices withdrawn. However, because a potential differential can exist between under the first control electrode 186 and under the floating gate 184, a charge packet 216 can remain under the floating gate 184 as a function of this potential difference. As discussed above in regard to FIGS. 3A-3D, the size of the charge packet 216 remaining under the floating gate 184 in this stage 266 can be a function of the voltage applied to the first control electrode 186 and the voltage manifesting on the floating gate 184 due to the ion concentration in the solution 108, and thus be a measure of the ion concentration in the solution 108, given a known voltage applied to the first control electrode 186.

Figures 8A, 8B, 8C, 8D:
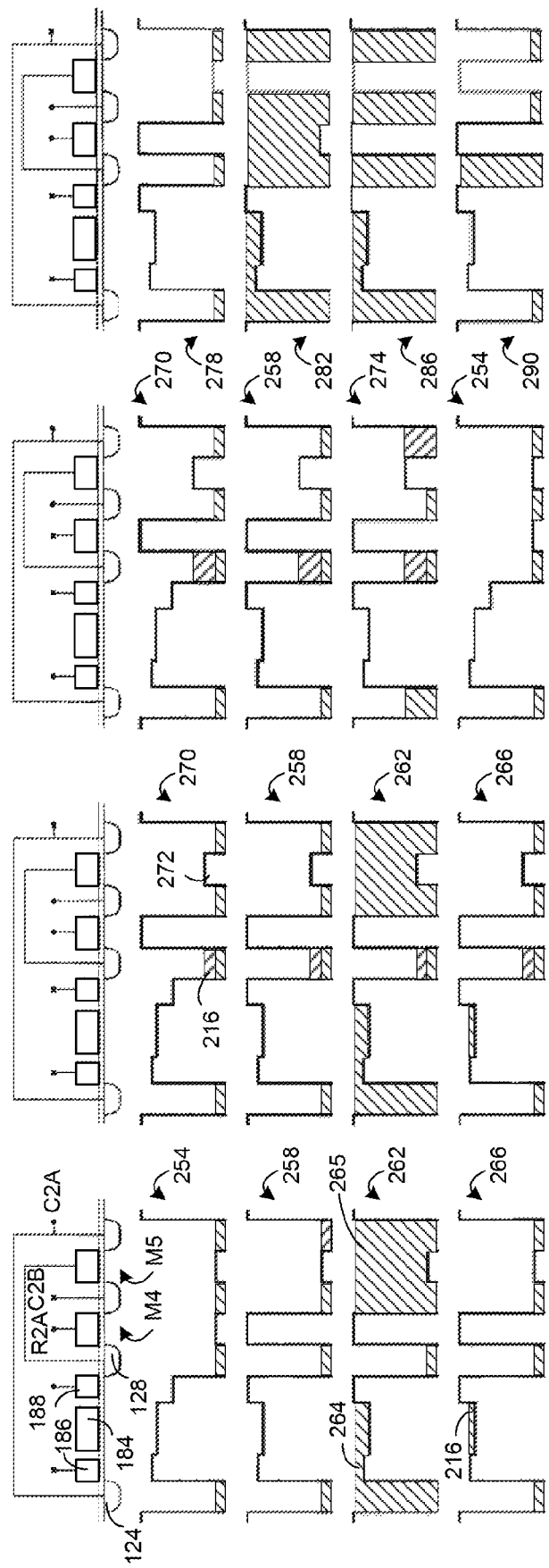
FIGS. 8A-8D are cross-sectional, potential and charge diagrams depicting embodiments of operation of the pixel circuit depicted in FIG. 7.

Finally, in a last phase 270 of the first operational cycle, depicted in FIG. 8B, the charge packet 216 remaining under the floating gate 184 after the third stage 266 of the cycle can be transferred from under the gate 184, through the region 232 under the second control electrode 188, and into the drain diffusion region 128, where it can be maintained, similar to as discussed above in regard to the first phase 220 of the operational cycle of FIGS. 3A-3D. The charge packet 216 can be transferred to the drain region 128 by lowering the potential barrier under the second control electrode 188 by delivering a logic high or high-valued voltage to the second control electrode 188. The charge delivered to the drain 128 of the charge accumulation device 104 incrementally decreases the voltage at this drain 128, and because the gate of the readout transistor M5 is connected to the drain 128, the charge packet 216 thus also incrementally increases the voltage at the gate of the readout transistor M5, as evidenced by the incrementally decreased potential barrier 272 under the gate of this readout transistor M5 at the end of the last stage 270 of the operational cycle. In this way, the voltage at and the potential under the gate of the readout transistor M5 can be a function of the charge packets 216 accumulated at the drain 128 of the charge accumulation device 104 at the end of every operational cycle.

FIGS. 8B-8C depict a second operational cycle, in which another charge packet is accumulated as in the first operational cycle depicted in FIGS. 8A-8B, with the result being the voltage at and the potential under the gate of the readout transistor again tracking the size of the plurality of accumulated charge packets 216. FIG. 8C also depicts another reset phase after the second operational cycle.

An output can be generated by sampling the voltage at the source of the readout transistor M5. This can occur during a readout phase 274. The output can also be generated using a double sampling technique in which both a first output and a second output is provided. The first output can represent an output produced by a background level of charge present at the drain 128 of the charge accumulation device 104. The second output can represent an output produced by a both the background level of charge and the plurality of charge packets 216 accumulated at the drain 128. Subtracting the first output from the second output can thus produce a more accurate measurement of the charge packets 216 accumulated to represent the ion concentration of the solution 108. In one embodiment, the first output can be sampled during the first phase 258 of the operational cycle. The second the second output can then be that sampled during the readout phase 274.

FIG. 8D also depicts an embodiment of a deactivation sequence for a row of the pixels of the embodiment 246a depicted in FIG. 7. In a first phase 278 of the deactivation sequence, a logic low or low-valued voltage is delivered to the row line R2A, while a logic high or high valued voltage is delivered to the first column line C2A. In a second phase 282 of the deactivation sequence, a logic high or high-valued voltage is delivered to the row line R2A, while the a logic low or low valued voltage is delivered to the first column line C2A. In a third phase 286 of the deactivation sequence, a logic low or low-valued voltage is delivered to the row line R2A, while the logic low or low valued voltage is maintained at the first column line C2A. In a fourth phase 290 of the deactivation sequence, a logic low or low-valued voltage is maintained on the row line R2A, while a logic high or high valued voltage is delivered to the first column line C2A.

Figure 9:
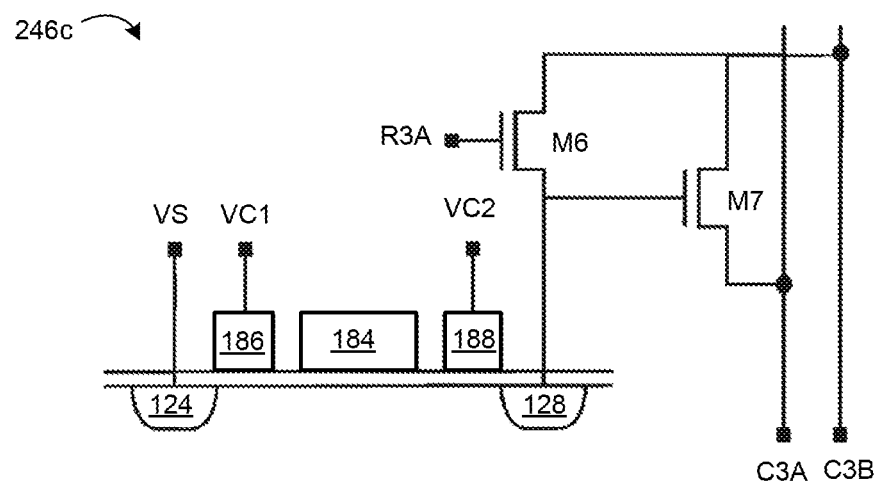
FIG. 9 is a partially cross-sectional, partially schematic diagram depicting another embodiment of a pixel circuit including the charge accumulation device and control and readout transistors.

FIG. 9 depicts another embodiment 246c of a two transistor, three electrode, or 2T3E, pixel. The control and readout circuit 112 can include two transistors, including a reset transistor M6 and a readout transistor M7, and the charge accumulation device 104 can have three electrodes, including the first and second control electrodes 186, 188 and the floating gate 184. The control and readout circuit 112 can receive a row line R3A and a plurality of column lines, including first and second column lines C3A, C3B. The reset transistor M6 can have a source connected to the drain 128 of the charge accumulation device 104, a gate connected to the row line R3A, and a drain connected to the second column line C3B. The readout transistor M7 can have a gate connected to the drain region 128 of the charge accumulation device 104 (and thus also the source of the reset transistor M6), a source connected to first column line C3A, and a drain connected to the second column line C3B. Turning on the reset transistor M6 can remove the charge packets 216 accumulated at the drain 128 of, and thus reset, the charge accumulation device 104, similarly to as discussed with respect to various embodiments above. With the reset transistor M6 turned off, the readout transistor M7 can provide an output voltage as a function of the charge packets 216 accumulated at the drain 128 of the charge accumulation device 104 operating in a source follower configuration, or provide an output current as a function of the charge packets 216 accumulated at the drain 128 of the charge accumulation device 104 operating in a common source configuration.

Figure 10:
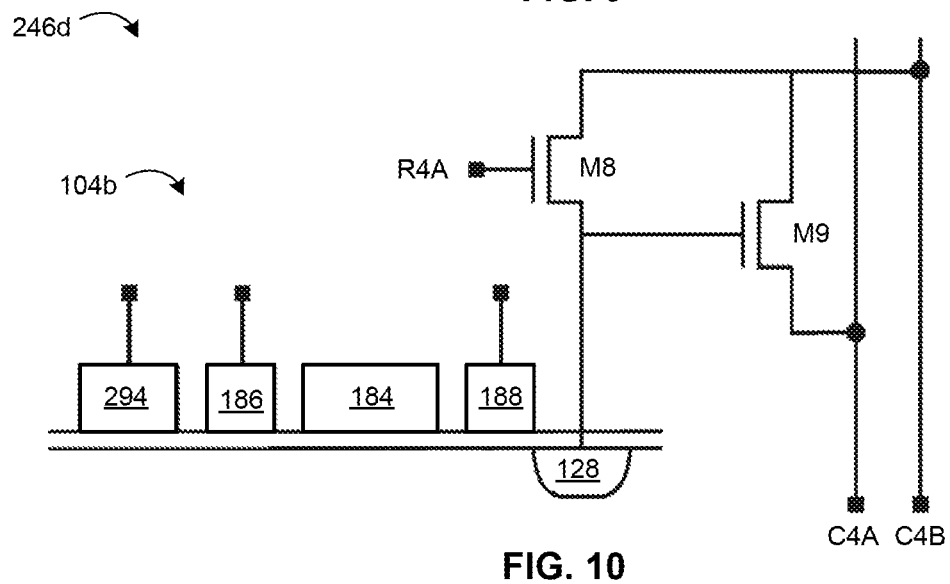
FIG. 10 is a partially cross-sectional, partially schematic diagram depicting another embodiment of a pixel circuit including the charge accumulation device and control and readout transistors.

The charge accumulation device 104 can also include more than two control electrodes. FIG. 10 depicts an embodiment of an ion-sensing pixel 246d having two control and readout transistors and four charge accumulation device electrodes, including three control electrodes and a floating gate. Although FIG. 10 depicts a simplified representation of the charge accumulation device 104b, actual embodiments can include other components of the charge accumulation device, such as components depicted in FIG. 2. The electrodes of the charge accumulation device 104b can include a first and second electrode 186, 294 on one side of the floating gate 184 and a third electrode 188 on the other side of the floating gate 184. The charge accumulation device 104b of FIG. 10 may not include a source region, but can include a drain region 128 adjacent to the region under the third electrode 188. The control and readout circuit 112 is the same as that depicted in FIG. 9, and can include two transistors, including a reset transistor M8 and a readout transistor M9, and receive a row line R4A and a plurality of column lines, including first and second column lines C4A, C4B. The reset transistor M8 can have a source connected to the drain 128 of the charge accumulation device 104b, a gate connected to the row line R4A, and a drain connected to the second column line C4B. The readout transistor M9 can have a gate connected to the drain region 128 of the charge accumulation device 104b (and thus also the source of the reset transistor M8), a source connected to first column line C4A, and a drain connected to the second column line C4B. The reset and readout transistors M8, M9 can operate as they can in the embodiment of FIG. 9.

FIGS. 11A-11D depict an embodiment of the operation of the pixel embodiment 246d of FIG. 10 to accumulate a plurality of charge packets 216 as a function of the solution ion concentration and generate an output signal as a function of the accumulated charge packets 216. FIGS. 11A-11D depict a plurality of complete cycles of an embodiment of operation of the charge accumulation device 104b. The top of each of FIGS. 11A-11D depicts a simplified partially cross-sectional, partially schematic representation of the charge-accumulation device 104b and control and readout transistors M8, M9 of FIG. 10. For convenience of illustration and explanation, other components of the charge-accumulation device 104b and control and readout transistors M8, M9 are omitted from the depictions, although omitted components can be present in actual embodiments. In each figure, below the representation of the charge-accumulation device 104b and control and readout transistors M8, M9 are four diagrams depicting, in a manner spatially aligned to the pixel representation above, potential energies and charge accumulation in the charge accumulation device 104b and control and readout transistors M8, M9 at different phases during the operational cycle of the pixel 246d.

In a reset phase 298 depicted in FIG. 11A, a potential gradient can be created from left to right under the first electrode 294, second electrode 186, floating gate 184 and third electrode 188, and a logic high or high-voltage value delivered to the gate of the reset transistor M8 to clear any charge from the charge accumulation device 104b remaining from previous operations.

In a first phase 302 of an operational cycle of the pixel 246d, the potential barrier under the third electrode 188 can then be raised higher than that in the reset phase 298 and that that existing on the floating gate 184. In a second phase 306 of the pixel operational cycle, charge can be injected into the charge accumulation device 104b through the drain diffusion node 128. In a third phase 310, the injected charge can be withdrawn from the charge accumulation device 104b, while a charge packet 216 remains under the floating gate 184 due to the potential barrier differential between the floating gate 184 and the third electrode 188 established in the second phase 306. In a fourth and final phase 314 of the operational cycle, a potential gradient can be created from right to left under the third electrode 188, floating gate 184, second electrode 186 and first electrode 186, to move the charge packet 216 from under the floating gate 184 to under the first electrode 294.

This accumulation cycle can then be repeated a plurality of times, as depicted in FIGS. 11B-11C, to accumulate a plurality of charge packets 216 under the first electrode 294.

FIG. 11D depicts a readout sequence to generate an output a signal based on the size of the plurality charge packets 216 accumulated under the first electrode 294. The readout sequence can incorporate a double sampling technique in which both a first output and a second output is provided. The first output can represent an output produced by a background level of charge present at the drain 128 of the charge accumulation device 104b. The second output can represent an output produced by a both the background level of charge and the plurality of charge packets 216 accumulated at the first electrode 294 after they have been transferred to the drain 128 of the charge accumulation device 104b. Subtracting the first output from the second output can thus produce a more accurate measurement of the charge packets 216 representing the measurement of the solution ion concentration. In a first phase 318 of the readout sequence, the first output can be provided by the readout transistor M9 while the plurality of charge packets 216 are still accumulated under the first electrode 294. In a second phase 322 of the readout sequence, a potential gradient can be created from left to right under the first electrode 294, second electrode 186, floating gate 184 and third electrode 188 to move the plurality of charge packets 216 from under the first electrode 294 to the drain 128 of the charge accumulation device 104b. After the second phase 322, in a third phase 326 of the readout sequence, the second output can be provided by the readout transistor M8.

FIG. 11D also depicts two phases 330, 334 of a deactivation sequence for a row of the pixel embodiments 246d of FIG. 10.

Variations on the above discussed embodiments are possible. Although embodiments of the charge accumulation device have been depicted and discussed herein as including n-type sources and drains, and p-type regions under the floating gate and control electrodes, in embodiments this relationship can also be reversed, with the charge accumulation device including p-type sources and drains, and n-type regions under the gate and control electrodes. Although FIG. 2 depicts an epitaxial p-type region under the control electrodes an floating gate, in embodiments a p-type or n-type region under the control electrodes and floating gate can include a diffusion region or other type of p-type or n-type region instead of or in addition to an epitaxial region. Although various control and readout transistors have been discussed herein as including NMOS transistors, in embodiments the control and readout transistors can include NMOS transistors, PMOS transistors, or any combination thereof. In some embodiments, rows and columns of pixels of the pixel array can share some or all of the row and column lines. Although in some embodiments discussed herein, charge carriers and charge packets have been assumed to be electrons, in other embodiments charge carriers and charge packets can comprise holes. Although stages of operational cycles of the charge accumulation device have been discussed herein as occurring in certain orders, and having certain labels (e.g., first phase, second phase, etc.), in other embodiments, the labels and stages of the operational cycles can be changed, rearranged, added to, subtracted to, etc. Although embodiments of the charge accumulation device have been discussed as having two or three control electrodes, in other embodiments, the charge accumulation device can have more or less than two or three control electrodes. Although certain embodiments of control signals have been depicted and discussed herein, in other embodiments, the various control signals can take different forms.

Additional embodiments of the charge accumulation device 104 and ion sensitive pixel 246 are also possible. For example, any feature of any of the embodiments of the charge accumulation device 104 and ion sensitive pixel 246 described herein can optionally be used in any other embodiment of the charge accumulation device 104 and ion sensitive pixel 246. Embodiments of the charge accumulation device 104 and ion sensitive pixel 246 can also optionally include any subset of the components or features of any embodiments of the charge accumulation device 104 and ion sensitive pixel 246 described herein.

Although the invention has been described above with reference to specific embodiments, the invention is not limited to the above embodiments and the specific configurations shown in the drawings. The operation processes are also not limited to those shown in the examples. Those skilled in the art will appreciate that the invention may be implemented in other ways without departing from the sprit and substantive features of the invention. The present embodiments are therefore to be considered in all respects as illustrative and not restrictive. The scope of the invention is indicated by the appended claims rather than by the foregoing description, and all changes that come within the meaning and range of equivalency of the claims are therefore intended to be embraced therein.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

What is claimed is:

1. An ion-sensitive circuit, comprising:
a charge-accumulation device to accumulate a plurality of charge packets as a function of an ion concentration of a fluid, including:
a substrate having formed thereon a gate oxide layer;
a first charge control electrode, formed over a first electrode semiconductor region and disposed on the gate oxide layer, to control entry of charge from the ion concentration of the fluid into a gate semiconductor region in response to a first control signal applied to the first electrode;
an electrically floating gate structure disposed between a gate semiconductor region and an ion-sensitive passivation surface configured to receive the fluid, the floating gate includes a plurality of conductors electrically coupled to one another and separated by dielectric layers; and
a second charge control electrode, formed over a second electrode semiconductor region and disposed on the gate oxide layer, to control transmission of the plurality of charge packets out of the gate semiconductor region and into a drain diffusion region in response to a second control signal applied to the second electrode; and
a drain diffusion region to receive the plurality of charge packets from the gate semiconductor region via the second electrode semiconductor region,
at least one control and readout transistor to generate an output voltage as a function of the accumulated plurality of charge packets at the drain diffusion region of the charge accumulation device, wherein the output voltage is representative of the ion concentration of the solution.

2. The ion-sensitive circuit of claim 1, further comprising a control circuit configured to generate and provide an injection control signal to inject charge into the gate semiconductor region through the first electrode semiconductor region.

3. The ion-sensitive circuit of claim 2, further comprising a source diffusion region adjacent to the first electrode semiconductor region, wherein the injection control signal includes a source control signal provided to the source diffusion region to inject the charge into the gate and first electrode semiconductor regions through the source diffusion region.

4. The ion-sensitive circuit of claim 1, further comprising a control circuit to generate and provide the second control signal to the second control electrode to individually transfer each of the plurality of charge packets from the gate semiconductor region one at a time, through the second electrode semiconductor region, to the drain diffusion region.

5. The ion-sensitive circuit of claim 1, further comprising a control circuit to generate a provide a readout control signal to the at least one readout transistor to generate the output signal after the plurality of the charge packets have been individually transferred one at a time from the gate semiconductor region to the drain diffusion region.

6. The ion-sensitive circuit of claim 1, wherein the charge accumulation device and the at least one readout transistor form a pixel circuit, and the ion-sensitive circuit further comprises a plurality of the pixel circuit arranged into an ion-sensitive pixel array.

7. The ion-sensitive circuit of claim 6, wherein the pixel array includes a plurality of rows and a plurality of columns of the pixel circuits, each row includes one or more row control and data lines, and each column includes one or more column control and data lines.

8. The ion-sensitive circuit of claim 1, further comprising a control circuit configured to control the charge accumulation device to individually transfer each of the plurality of charge packets from the gate semiconductor region, through the second electrode semiconductor region and to the drain diffusion region, at a selectable charge packet accumulation frequency.

9. The ion-sensitive circuit of claim 1, further comprising a control circuit configured to control the charge accumulation device and at least one readout transistor to generate the output signal as a function of the plurality of charge packets accumulated at the drain diffusion region at a selectable output generation frequency.

10. The ion-sensitive circuit of claim 1, wherein the at least one control and readout transistor includes:
a reset transistor connected to the drain diffusion region of the charge accumulation device, to a row control line and to a column control line; and
first and second readout transistors connected to the drain diffusion region of the charge accumulation device, to the column control line and to a column data line, wherein the first readout transistor is connected in a source follower configuration and the second readout transistor is connected in a cascode configuration.

11. The ion-sensitive circuit of claim 1, wherein the at least one control and readout transistor includes:
a reset transistor connected to the drain diffusion region of the charge accumulation device, to a row control line and to a column control line; and
a readout transistor connected to the drain diffusion region of the charge accumulation device, to a source diffusion region of the charge accumulation device, to the column control line and to a column data line.

12. The ion-sensitive circuit of claim 1, wherein the at least one control and readout transistor includes:
a reset transistor connected to the drain diffusion region of the charge accumulation device, to a row control line and to a column control line; and
a readout transistor connected to the drain diffusion region of the charge accumulation device, to the column control line and to a column data line.

13. The ion-sensitive circuit of claim 1, wherein the charge accumulation device includes a source diffusion region adjacent to the first electrode semiconductor region, the first electrode semiconductor region is adjacent to the gate semiconductor region, the gate electrode semiconductor region is adjacent to the second electrode semiconductor region, and the second electrode semiconductor region is adjacent to the drain diffusion region.

14. The ion-sensitive circuit of claim 1, wherein the charge accumulation device includes a third charge control electrode, above a third electrode semiconductor region, to control the accumulation of the plurality of charge packets in the third electrode semiconductor region before the plurality of charge packets are transferred to the drain diffusion region.

* * * * *

UNITED STATES PATENT AND TRADEMARK OFFICE
CERTIFICATE OF CORRECTION

PATENT NO. : 8,858,782 B2
APPLICATION NO. : 13/173146
DATED : October 14, 2014
INVENTOR(S) : Keith Fife It is certified that error appears in the above-identified patent and that said Letters Patent is hereby corrected as shown below:

In the Claims,

Claim 5, Column 20, Line 58, following "a control circuit to" and before "provide a readout control signal" delete "generate a".

Signed and Sealed this
Twenty-fourth Day of February, 2015

Michelle K. Lee
*Deputy Director of the United States Patent and Trademark Office*